United States Patent
Hsieh et al.

(10) Patent No.: US 11,246,883 B2
(45) Date of Patent: Feb. 15, 2022

(54) MICRORNA LET-7 AND TRANSFORMING GROWTH FACTOR BETA RECEPTOR III AXIS AS TARGET FOR CARDIAC INJURIES

(71) Applicant: Academia Sinica, Taipei (TW)

(72) Inventors: Patrick C. H. Hsieh, Taipei (TW); Chen-Yun Chen, Taipei (TW); Yu-Che Cheng, Taichung (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 16/337,583

(22) PCT Filed: Sep. 29, 2017

(86) PCT No.: PCT/US2017/054376
§ 371 (c)(1),
(2) Date: Mar. 28, 2019

(87) PCT Pub. No.: WO2018/064515
PCT Pub. Date: Apr. 5, 2018

(65) Prior Publication Data
US 2019/0275070 A1    Sep. 12, 2019

Related U.S. Application Data

(60) Provisional application No. 62/402,255, filed on Sep. 30, 2016.

(51) Int. Cl.
| | | |
|---|---|---|
| *A61K 31/7105* | (2006.01) | |
| *A61K 9/00* | (2006.01) | |
| *C07K 16/28* | (2006.01) | |
| *C12N 15/113* | (2010.01) | |
| *A61K 48/00* | (2006.01) | |
| *A61K 39/00* | (2006.01) | |

(52) U.S. Cl.
CPC ........ *A61K 31/7105* (2013.01); *A61K 9/0019* (2013.01); *A61K 9/0053* (2013.01); *A61K 48/00* (2013.01); *C07K 16/2863* (2013.01); *C12N 15/113* (2013.01); *C12N 15/1138* (2013.01); *A61K 2039/505* (2013.01); *C12N 2310/141* (2013.01); *C12N 2320/31* (2013.01)

(58) Field of Classification Search
None
See application file for complete search history.

(56) References Cited

U.S. PATENT DOCUMENTS

| | | |
|---|---|---|
| 5,981,568 A | 11/1999 | Kunz et al. |
| 2004/0258689 A1 | 12/2004 | Vale et al. |
| 2012/0282696 A1 | 11/2012 | Johnson et al. |
| 2012/0316240 A1 | 12/2012 | Song et al. |

FOREIGN PATENT DOCUMENTS

| | | |
|---|---|---|
| CN | 101675165 | 3/2010 |
| CN | 101675165 A | 3/2010 |
| WO | 2000/053211 A2 | 9/2000 |

OTHER PUBLICATIONS

Tolonen et al. Pharm Res Per, 2014, vol. 2, No. 4, e00056 (14 pages).*
Seeger et al. Journal of Molecular and Cellular Cardiology 2016, vol. 94, pp. 145-152.*
Sun et al. J Am Heart Assoc. 2017, vol. 6, p. e005357 (16 pages).*
Joshi et al. Biochimica et Biophysica Acta 2016, vol. 1862, pp. 240-251.*
Liang et al., A novel reciprocal loop between microRNA-21 and TGFβRIII is involved in cardiac fibrosis. Int J Biochem Cell Biol. Dec. 2012;44(12):2152-60. doi:10.1016/j.biocel.2012.08.019. Epub Sep. 5, 2012.
Kurakula et al., Regulatory RNAs controlling vascular (dys)function by affecting TGF-β family signalling. EXCLI J. Jul. 10, 2015;14:832-50. doi: 10.17179/excli2015-423. eCollection 2015.
[No Author Listed], Antibodies. Accessible at http://www.bioinf.org.uk/abs/. 2015-2019. Accessed on Feb. 5, 2020. 5 pages.
[No Author Listed], *Homo sapiens* chromosome 1, GRCh38.p13 Primary Assembly. NCBI Reference Sequence: NC_000001.11. Nov. 22, 2020. Accessible at https://www.ncbi.nlm.nih.gov/nuccore/nc_000001.11. 3 pages.
[No Author Listed], *Homo sapiens* chromosome 6, GRCh38.p13 Primary Assembly. NCBI Reference Sequence: NC_000006.12. Accessible at https://www.ncbi.nlm.nih.gov/nuccore/nc_000006.12. Nov. 22, 2020. 3 pages.
Almagro, Identification of differences in the specificity-determining residues of antibodies that recognize antigens of different size: implications for the rational design of antibody repertoires. J Mol Recognit. Mar.-Apr. 2004;17(2):132-43. doi: 10.1002/jmr.659.
Bilandzic et al., Betaglycan: a multifunctional accessory. Mol Cell Endocrinol. Jun. 6, 2011;339(1-2):180-9. doi: 10.1016/j.mce.2011.04.014. Epub Apr. 28, 2011.
Cao et al., microRNA expression profiling of the developing mouse heart. Int J Mol Med. Nov. 2012;30(5):1095-104. doi: 10.3892/ijmm.2012.1092. Epub Aug. 9, 2012.
Chothia et al., Structural repertoire of the human VH segments. J Mol Biol. Oct. 5, 1992;227(3):799-817. doi: 10.1016/0022-2836(92)90224-8.

(Continued)

*Primary Examiner* — Tracy Vivlemore
(74) *Attorney, Agent, or Firm* — Wolf, Greenfield & Sacks, P.C.

(57) ABSTRACT

Methods for ameliorating cardiac is juries such as myocardial infarction by either enhancing the activity of a let-7 microRNA or inhibiting the activity of transformation growth factor beta receptor III (T GFBR3). Also provided herein are assay methods for detecting the level of TGFBR3, the level of a let-7 microRNA, or both in a biological sample.

21 Claims, 10 Drawing Sheets

Specification includes a Sequence Listing.

(56) References Cited

OTHER PUBLICATIONS

Copley et al., The Lin28b-let-7-Hmga2 axis determines the higher self-renewal potential of fetal haematopoietic stem cells. Nat Cell Biol. Aug. 2013;15(8):916-25. doi: 10.1038/ncb2783. Epub Jun. 30, 2013.

Cortez et al., MicroRNAs in body fluids—the mix of hormones and biomarkers. Nat Rev Clin Oncol. Jun. 7, 2011;8(8):467-77. doi: 10.1038/nrclinonc.2011.76.

El Azzouzi et al., The hypoxia-inducible microRNA cluster miR-199a~214 targets myocardial PPARd and impairs mitochondrial fatty acid oxidation. Cell Metab. Sep. 3, 2013;18(3):341-54. doi: 10.1016/j.cmet.2013.08.009.

Gurha et al., Targeted deletion of microRNA-22 promotes stress-induced cardiac dilation and contractile dysfunction. Circulation. Jun. 5, 2012;125(22):2751-61. doi: 10.1161/CIRCULATIONAHA.111.044354. Epub May 8, 2012.

Huang et al. MicroRNA-22 regulates cardiac hypertrophy and remodeling in response to stress. Circ Res. Apr. 26, 2013;112(9):1234-43. doi: 10.1161/CIRCRESAHA.112.300682. Epub Mar. 22, 2013.

Iliopoulos et al., An epigenetic switch involving NF-kappaB, Lin28, Let-7 MicroRNA, and IL6 links inflammation to cell transformation. Cell. Nov. 13, 2009;139(4):693-706. doi: 10.1016/j.cell.2009.10.014. Epub Oct. 29, 2009.

Kuppusamy et al., Let-7 family of microRNA is required for maturation and adult-like metabolism in stem cell-derived cardiomyocytes. Proc Natl Acad Sci U S A. May 26, 2015;112(21):E2785-94. doi: 10.1073/pnas.1424042112. Epub May 11, 2015.

Kurakula et al., Regulatory RNAs controlling vascular (dys)function by affecting TGF-β family signalling. EXCLI J. Jul. 10, 2015;14:832-50. doi: 10.17179/excli2015-423.

Li et al., miR-199a impairs autophagy and induces cardiac hypertrophy through mTOR activation. Cell Death Differ. Jul. 2017;24(7):1205-1213. doi: 10.1038/cdd.2015.95. Epub Jul. 10, 2015.

Matkovich et al., RISC RNA sequencing for context-specific identification of in vivo microRNA targets. Circ Res. Jan. 7, 2011; 108(1): 18-26. doi: 10.1161/CIRCRESAHA.110.233528. Epub Oct. 28, 2010.

Mayr et al., Disrupting the pairing between let-7 and Hmga2 enhances oncogenic transformation. Science. Mar. 16, 2007;315(5818):1576-9. doi: 10.1126/science.1137999. Epub Feb. 22, 2007.

Meunier et al., Birth and expression evolution of mammalian microRNA genes. Genome Res. Jan. 2013;23(1):34-45. doi: 10.1101/gr.140269.112. Epub Oct. 3, 2012.

Pan et al., MicroRNA-101 inhibited postinfarct cardiac fibrosis and improved left ventricular compliance via the FBJ osteosarcoma oncogene/transforming growth factor-β1 pathway. Circulation. Aug. 14, 2012;126(7):840-50. doi: 10.1161/CIRCULATIONAHA.112.094524. Epub Jul. 18, 2012.

Ren et al., Role of p38alpha MAPK in cardiac apoptosis and remodeling after myocardial infarction. J Mol Cell Cardiol. Apr. 2005;38(4):617-23. doi: 10.1016/j.yjmcc.2005.01.012.

Roos et al., A Small-Molecule Inhibitor of Lin28. ACS Chem Biol. Oct. 21, 2016;11(10):2773-2781. doi: 10.1021/acschembio.6b00232. Epub Aug. 22, 2016.

Roush et al., The let-7 family of microRNAs. Trends Cell Biol. Oct. 2008;18(10):505-16. doi: 10.1016/j.tcb.2008.07.007. Epub Sep. 4, 2008.

Rustagi et al., Comparative Characterization of Cardiac Development Specific microRNAs: Fetal Regulators for Future. PLoS One. Oct. 14, 2015;10(10):e0139359. doi: 10.1371/journal.pone.0139359.

Seeger et al., Inhibition of let-7 augments the recruitment of epicardial cells and improves cardiac function after myocardial infarction. J Mol Cell Cardiol. May 2016;94:145-152. doi: 10.1016/j.yjmcc.2016.04.002. Epub Apr. 9, 2016.

Shin et al., Expanding the microRNA targeting code: functional sites with centered pairing. Mol Cell. Jun. 25, 2010;38(6):789-802. doi: 10.1016/j.molcel.2010.06.005.

Tay et al., Aberrant ceRNA activity drives lung cancer. Cell Res. Mar. 2014;24(3):259-60. doi: 10.1038/cr.2014.21. Epub Feb. 14, 2014.

Thornton et al., How does Lin28 let-7 control development and disease? Trends Cell Biol. Sep. 2012;22(9):474-82. doi: 10.1016/j.tcb.2012.06.001. Epub Jul. 9, 2012.

Tzur et al., Comprehensive gene and microRNA expression profiling reveals a role for microRNAs in human liver development. PLoS One. Oct. 20, 2009;4(10):e7511. doi: 10.1371/journal.pone.0007511.

Varga et al., MicroRNAs associated with ischemia-reperfusion injury and cardioprotection by ischemic pre- and postconditioning: protectomiRs. Am J Physiol Heart Circ Physiol. Jul. 15, 2014;307(2):H216-27. doi: 10.1152/ajpheart.00812.2013. Epub May 23, 2014.

Wang et al., MicroRNA-103/107 Regulate Programmed Necrosis and Myocardial Ischemia/Reperfusion Injury Through Targeting FADD. Circ Res. Jul. 31, 2015;117(4):352-63. doi: 10.1161/CIRCRESAHA.117.305781. Epub Jun. 2, 2015.

Yang et al., Thioredoxin 1 negatively regulates angiotensin II-induced cardiac hypertrophy through upregulation of miR-98/let-7. Circ Res. Feb. 4, 2011; 108(3):305-13. doi: 10.1161/CIRCRESAHA.110.228437. Epub Dec. 23, 2010.

Zhu et al., The Lin28/let-7 axis regulates glucose metabolism. Cell. Sep. 30, 2011; 147(1):81-94. doi: 10.1016/j.cell.2011.08.033.

* cited by examiner

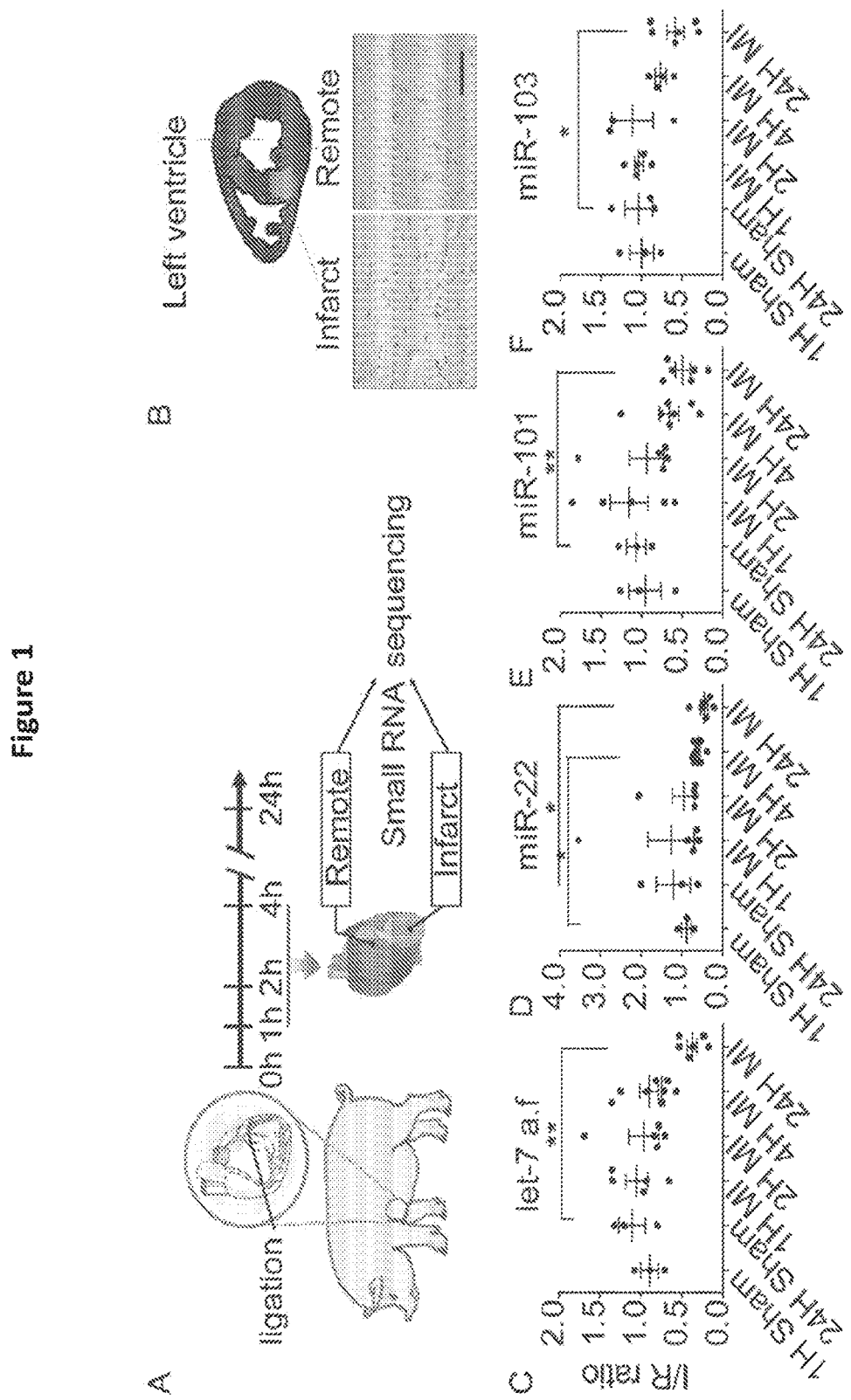

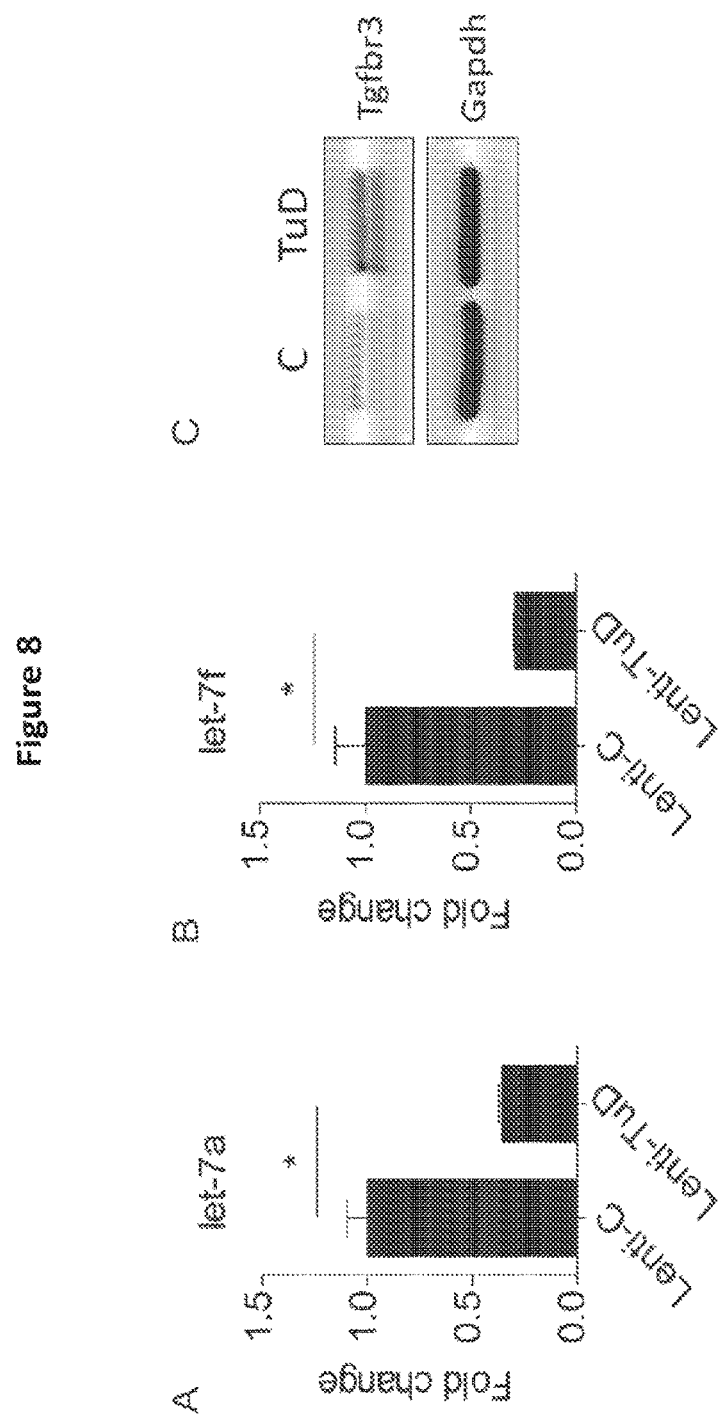

MICRORNA LET-7 AND TRANSFORMING GROWTH FACTOR BETA RECEPTOR III AXIS AS TARGET FOR CARDIAC INJURIES

RELATED APPLICATIONS

This application is a national stage filing under 35 U.S.C. § 371 of International Patent Application Serial No. PCT/US2017/054376, filed Sep. 29, 2017, entitled "MICRORNA LET-7 AND TRANSFORMING GROWTH FACTOR BETA RECEPTOR III AXIS AS TARGET FOR CARDIAC INJURIES," which claims the benefit of the filing date of U.S. Provisional Application No. 62/402,255, filed on Sep. 30, 2016, entitled "MICRORNA LET-7 AND TRANSFORMING GROWTH FACTOR BETA RECEPTOR III AXIS AS TARGET FOR CARDIAC INJURIES," the content of each of which is herein incorporated by reference in its entirety.

BACKGROUND OF INVENTION

Disruption of normal cardiac myocyte membrane integrity can lead to cardiac injury. Loss of the cardiac myocyte membrane integrity can be determined by detecting a variety of biological metabolites, microRNAs, and proteins such as troponin, mir-1, mir-133a/b, mir-499 a, miR-22, miR-101, miR-103 and miR-199a-3p, creatine kinase, myoglobin, heart-type fatty acid binding protein, and/or lactate dehydrogenase.

Cardiac injuries may be caused by trauma, toxins, and viral infection. Cardiac ischemia or infarction, resulting from an imbalance between the supply and demand of oxygen (and nutrients), is the most common cause for cardiac injuries.

Myocardial infarction (MI), caused by the blockage of coronary artery, is a leading cause of death worldwide. Several biomarkers are used to evaluate heart function after myocardial infarction, such as Troponin and BNP. Although Troponin can be detected within 14 days, the expression peak occurs within three days, which makes it difficult to evaluate the progression of the disease. Morrow et al. Circulation, 115(13):e356-375; 2007. Combining more markers will assist in the diagnosis of cardiac injury.

SUMMARY OF INVENTION

One aspect of the present disclosure provides a method for treating a cardiac injury, comprising administering to a subject in need thereof an effective amount of a let-7 enhancer or TGFBR3 inhibitor. In some embodiments, the cardiac injury involves myocardial infarction, an acute coronary syndrome, myocarditis, cardiomyopathy, a post-operation injury, or a combination thereof.

In some embodiments, the TGFBR3 inhibitor can be an antibody binding to TGFBR3 or an interfering RNA (RNAi) that suppresses the expression of TGFBR3. Such an antibody may specifically bind glycosylated TGFBR3, for example, specifically bind an N-terminal epitope of TGFBR3, which may be glycosylated. In some examples, the antibody binds to a transmembrane-cytoplasmic region of TGFBR3, e.g., binding to SEQ ID NO:2. The antibody used in the methods described herein may be a full-length antibody or an antigen-binding fragment thereof. Alternatively or in addition, the antibody is a human antibody, a humanized antibody, a chimeric antibody, or a single-chain antibody.

In some examples, the anti-TGFBR3 antibody for use in any of the methods described herein binds the same epitope of TGFBR3 as Anti-RIII-1 antibody (described below) or competes again Anti-RIII-1 antibody from binding to TGFBR3. In some instances, the anti-TGFBR3 antibody comprises the same heavy chain and/or light chain complementary determining regions (CDRs) as Anti-RIII-1 antibody. In one example, the anti-TGFBR3 comprises the same heavy chain variable ($V_H$) region and/or the same light chain variable ($V_L$) region as Anti-RIII-1 antibody (SEQ ID NO:95 and SEQ ID NO:96, respectively).

In some embodiments, the let-7 enhancer is a let-7 nucleic acid. Such a nucleic acid may comprise the nucleotide sequence of SEQ ID NO: 94. In other embodiments, the let-7 enhancer can be a Lin28 inhibitor.

The subject to be treated by any of the methods described herein may be a human patient having or suspected of having a cardiac injury as described herein. In some examples, the subject is a human patient having or suspected of having myocardial infarction. In some examples, the subject may have an elevated level of TGFBR3, a reduced level of let-7, or both as compared to a subject not suffering from the cardiac injury.

In any of the methods described herein, the let-7 enhancer and/or the TGFBR3 inhibitor is delivered by a systemic route or by a local route, such as intramyocardial injection or intracoronary injection.

In another aspect, the present disclosure provides a method for detecting the presence of TGFBR3 in a biological sample. Such a method may comprise: (i) providing a biological sample suspected of containing TGFBR3, (ii) contacting the biological sample with an antibody that binds a cleaved form of TGFBR3, which may be SEQ ID NO: 3, to form a complex of the antibody and the cleaved form of TGFBR3, (iii) measuring the level of the cleaved form of TGFBR3 in the biological sample based on the level of the complex; and (iv) determining presence or absence of TGFBR3 in the biological sample. In some examples, the antibody used in any of the assay methods described herein may specifically bind glycosylated SEQ ID NO: 3. Such an antibody may bind an N-terminal epitope of SEQ ID NO: 3. The epitope may be glycosylated.

The biological sample may be obtained from a human subject suspected of having a cardiac injury. Such a biological sample may be a serum sample or a plasma sample.

Any of the assay methods described herein may further comprise measuring the level of let-7 in the biological sample. Alternatively or in addition, the method may further comprise assessing whether the subject, from whom the biological sample is obtained, has or is at risk for cardiac injuries based on the level of the cleaved form of TGFBR3, the level of let-7, or both in the biological sample. If the subject is determined as having or at risk for the cardiac injury, a cardiac injury therapy can be performed on the subject.

Also within the scope of the present disclosure are (i) pharmaceutical compositions for use in treating a cardiac injury as described herein, wherein the pharmaceutical composition comprises a TGFBR3 inhibitor, a let-7 enhancer, or both and a pharmaceutically acceptable carrier; and (ii) use of either the TGFBR3 inhibitor or the let-7 enhancer in manufacturing a medicament for use in treating the cardiac injury.

The details of one or more embodiments of the invention are set forth in the description below. Other features or advantages of the present invention will be apparent from

BRIEF DESCRIPTION OF DRAWINGS

FIG. 8 shows Tough Decoy RNA inhibited let-7a and let-7f expression and de-repressed the expression of Tgfbr3. Rat neonatal cardiomyocytes were infected by lentiviruses carrying Tough Decoy (TuD) RNA. After antibiotic selection to remove non-infected cells, RNA and protein were extracted for TaqMan qPCR and Western Blot analysis. Panel A: Let-7a was repressed by TuD RNA expression (n=2). Panel B: Let-7f was repressed by TuD RNA expression (n=2). Panel C: Tgfbr3 was upregulated after TuD RNA expression.

DETAILED DESCRIPTION OF INVENTION

Figure 1:
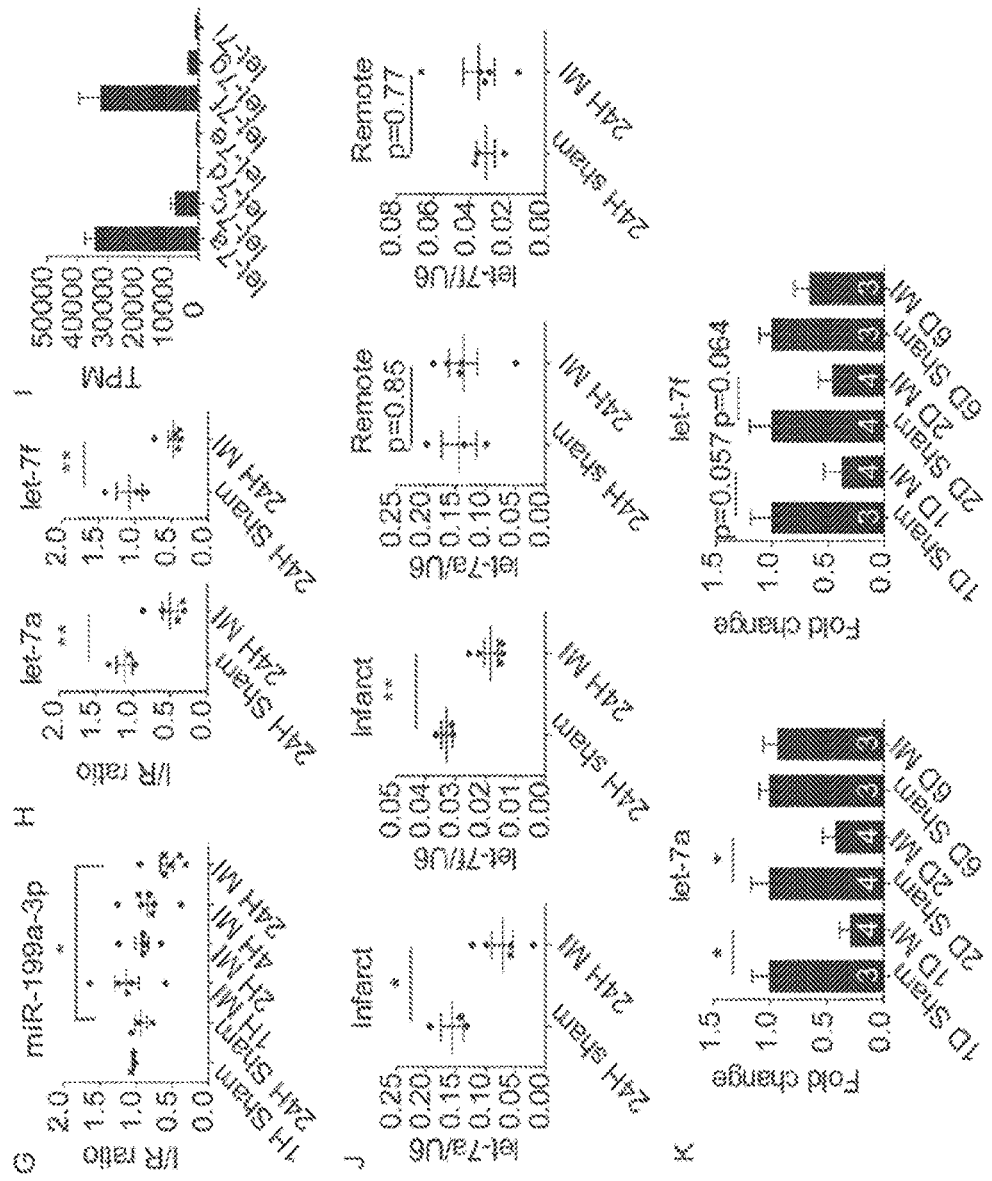
FIG. 1 shows microRNA let-7a and let-7f response to early myocardial infarction. Panel A: Experimental design. Pigs were subjected to LAD ligation for 1, 2 and 4 hours. RNA was extracted from both infarct and remote tissues and was subjected to next-generation sequencing. Panel B: Tunel staining of pig tissues showed apoptosis cells in infarct area of heart 24 hr-post myocardial infarction. Bar: 100 mm. Panels C-G: Stem-loop qPCR validation of miRNA expression in 1 h sham, 24 h sham, 1 h, 2 h, 4 h and 24 h post-MI pig hearts. An I/R ratio indicates miRNA expression level in the infarct area to that in the remote area. A remote area is considered as internal control for each individual pig. microRNA let-7a.f, miR-101, miR-103 and miR199a-3p were significantly downregulated 24 h post MI. miR-22 was downregulated since 4 h post MI. Panel H: TaqMan qPCR validation of let-7a and let-7f expression in pig hearts. Panel I: Abundance of let-7 family in pig hearts by next generation sequencing data from remote area of three individual pigs. TPM: transcripts per million. Panel J: Let-7a and let-7f expression level compared to U6 in the infarct and remote areas 24 hours post MI. Panel K: Downregulation of let-7a and let-7f was found one and two days post MI in the mouse model.

Acute myocardial infarction (MI) is caused by the blockage of coronary artery and leads to the death of ischemic cardiomyocytes (Senter et al., *Cleve Clin J Med* 76, 159-166 (2009)). The present study reveals that let-7 microRNAs such as let-7a and let-7f are significant effectors as identified in a porcine MI model using next-generation sequencing (NGS). Although let-7 is one of the early discovered microRNA and is abundant and conserved from *C. elegans* to mammals (Roush et al., *Trends Cell Biol* 18, 505-516 (2008)), little is known about the function of let-7 in myocardial infarction. Further, the present study reveals the downstream target gene of let-7, TGFBR3, and the potential function of let-7. Surprisingly, both plasma let-7 and TGFBR3 were found to respond to myocardial infarction. These results indicate that the microRNA let-7/TGFBR3 axis plays an important role in cardiac injury such as MI, suggesting that let-7 and TGFBR3, either alone or taken together, can serve as reliable disease target in both treatment and diagnosis/prognosis of cardiac injuries.

Accordingly, provided herein are methods for treating cardiac injuries by blocking the TGFBR3 activity and/or enhancing the let-7 activity and assay methods for measuring the level of TGFBR3 and/or the level of let-7 in a biological samples. Results obtained from such assay methods can be used for various purposes, including assessing presence and/or risk for a cardiac injury.

I. Treating Cardiac Injuries

Provided herein are methods for treating cardiac injuries, the methods comprising administering to a subject in need thereof an effective amount of a TGFBR3 inhibitor, a let-7 enhancer, or a combination thereof.

(A) TGFBR3 Inhibitors

TGFBR3, also known as betaglycan, is a membrane proteoglycan that binds to various members of the TGF-β superfamily of ligands via its heparin sulfate chains. It often acts as a coreceptor with TGF-β superfamily members. It is involved in the apoptotic pathways in synovial fibroblasts and GPCR pathway. TGFBR3 proteins and genes encoding such from a suitable species (e.g., human, rat, mouse and pig) are well known in the art. For example, exemplary human TGFBR3 protein and gene sequences can be found under GenBank Accession Nos. Q03167 and XM_006710868.2, the relevant disclosures therein are incorporated by reference herein.

The amino acid sequence of an exemplary mature human TGFBR3 is provided below (SEQ ID NO:1):

GPEPGALCELSPVSASHPVQALMESFTVLSGCASRGTTGLPQEVHVLNLR

TAGQGPGQLQREVTLHLNPISSVHIHHKSVVFLLNSPHPLVWHLKTERLA

TGVSRLFLVSEGSVVQFSSANFSLTAETEERNFPHGNEHLLNWARKEYGA

-continued
VTSFTELKIARNIYIKVGEDQVFPPKCNIGKNFLSLNYLAEYLQPKAAEG

CVMSSQPQNEEVHIIELITPNSNPYSAFQVDITIDIRPSQEDLEVVKNLI

LILKCKKSVNWVIKSFDVKGSLKIIAPNSIGFGKESERSMTMTKSIRDDI

PSTQGNLVKWALDNGYSPITSYTMAPVANRFHLRLENNAEEMGDEEVHTI

PPELRILLDPGALPALQNPPIRGGEGQNGGLPFPFPDISRRVWNEEGEDG

LPRPKDPVIPSIQLFPGLREPEEVQGSVDIALSVKCDNEKMIVAVEKDSF

QASGYSGMDVTLLDPTCKAKMNGTHFVLESPLNGCGTRPRWSALDGVVYY

NSIVIQVPALGDSSGWPDGYEDLESGDNGFPGDMDEGDASLFTRPEIVVF

NCSLQQVRNPSSFQEQPHGNITFNMELYNTDLFLVPSQGVFSVPENGHVY

VEVSVTKAEQELGFAIQTCFISPYSNPDRMSHYTIIENICPKDESVKFYS

PKRVHFPIPQADMDKKRFSFVFKPVFNTSLLFLQCELTLCTKMEKHPQKL

PKCVPPDEACTSLDASIIWAMMQNKKTFTKPLAVIHHEAESKEKGPSMKE

PNPISPPIFHGLDTLTV*MGIAFAAFVIGALLTGALWYIYSHTGETAGRQQ*

*VPTSPPASENSSAAHSIGSTQSTPCSSSSTA*

The C-terminal italic region refers to the transmembrane-cytoplasmic domain (SEQ ID NO:2) and the N-terminal boldfaced region refers to the extracellular domain (SEQ ID NO:3).

The TGFBR3 inhibitors to be used in the methods described herein are molecules that block, suppress, or reduce (including significant blockage, suppression or reduction) the biological activity of TGFBR3, including downstream pathways mediated by TGFBR3. The term "inhibitor" implies no specific mechanism of biological action whatsoever, and is deemed to expressly include and encompass all possible pharmacological, physiological, and biochemical interactions with TGFBR3 whether direct or indirect. For the purpose of the present disclosure, it will be explicitly understood that the term "inhibitor" encompasses all the previously identified terms, titles, and functional states and characteristics whereby the TGFBR3 itself (e.g., human TGFBR3), a TGFBR3 biological activity (including but not limited to its ability to mediate cardiomyocyte death), or the consequences of the biological activity, are substantially nullified, decreased, or neutralized in any meaningful degree, e.g., by at least 20%, 50%, 70%, 85%, 90%, 100%, 150%, 200%, 300%, or 500%, or by 10-fold, 20-fold, 50-fold, 100-fold, 1000-fold, or $10^4$-fold.

Exemplary TGFBR3 inhibitors include, but are not limited to, an anti-TGFBR3 antibody, an anti-sense nucleic acid molecule directed to a TGFBR3 (including an anti-sense nucleic acid directed to a nucleic acid encoding TGFBR3), a small interfering RNA (siRNA) directed toward a TGFBR3 nucleic acid, a microRNA directed toward a TGFBR3 nucleic acid, a TGFBR3 nucleic acid aptamer, or a TGFBR3 inhibitory compound.

Antibodies Binding to TGFBR3

In some embodiments, the TGFBR3 inhibitor is an antibody that binds to and inhibits the TGFBR3 biological activity and/or downstream pathway(s) mediated by TGFBR3 signaling. In some examples, an anti-TGFBR3 antibody used in the methods described herein suppresses a TGFBR3-associated signaling pathway by at least 20%, at least 40%, at least 50%, at least 75%, at least 90%, at least 100%, or by at least 2-fold, at least 5-fold, at least 10-fold, at least 20-fold, at least 50-fold, at least 100-fold, or at least 1000-fold. In some embodiments, the anti-TGFBR3 antibody binds to an extracellular domain of TGFBR3 (e.g., SEQ ID NO: 3). In other embodiments, the anti-TGFBR3 antibody binds to a domain within the transmembrane-cytoplasmic region of a TGFBR3 (e.g., SEQ ID NO: 2).

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')$_2$, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The antibodies to be used in the methods described herein can be murine, rat, human, or any other origin (including chimeric or humanized antibodies). In some examples, the antibody comprises a modified constant region, such as a constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in Eur. J. Immunol. (1999) 29:2613-2624; PCT Application No. PCT/GB99/01441; and/or UK Patent Application No. 9809951.8.

Any of the antibodies described herein can be either monoclonal or polyclonal. A "monoclonal antibody" refers to a homogenous antibody population and a "polyclonal antibody" refers to a heterogeneous antibody population. These two terms do not limit the source of an antibody or the manner in which it is made.

In one example, the antibody used in the methods described herein is a humanized antibody. Humanized antibodies refer to forms of non-human (e.g., murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation.

In another example, the antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

The antibody disclosed herein may specifically bind a target or epitope, such as human TGFBR3. An antibody that "specifically binds" (used interchangeably herein) to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically (or preferentially) binds to a TGFBR3 epitope is an antibody that binds this TGFBR3 epitope with greater affinity, avidity, more readily, and/or with greater duration than it binds to other TGFBR3 epitopes or non-TGFBR3 epitopes. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

In some examples, the antibodies for use in the method described herein may specifically bind membrane-bound TGFBR3. Such an antibody may be capable of recognizing and binding to a TGFBR3 epitope exposed on the surface of cells expressing this receptor. In some examples, an anti-TGFBR3 antibody for use in the method described herein may specifically bind the extracellular domain of a TGFBR3, e.g., SEQ ID NO: 3. In other examples, an anti-TGFBR3 antibody for use in the method described herein may bind to the transmembrane-cytoplasmic domain of a TGFBR3, for example, SEQ ID NO: 2. In yet other examples, the anti-TGFBR3 antibody for use in the method described herein may specifically bind a TGFBR3 or a fragment thereof, which is glycosylated. For example, the antibody may specifically bind to an N-terminal fragment of TGFBR3 that is glycosylated. In some embodiments, the glycosylation sites include, but are not limited to 141 N-linked (GlcNAc . . . ), 369 O-linked (GalNAc . . . ), 492 N-linked (GlcNAc . . . ), 534 O-linked (Xyl . . . ) (glycosaminoglycan), 545 O-linked (Xyl . . . ) (glycosaminoglycan), 571 N-linked (GlcNAc . . . ), 590 N-linked (GlcNAc . . . ), and 697 N-linked (GlcNAc . . . ).

The binding affinity of an anti-TGFBR3 antibody to TGFBR3 (such as human TGFBR3) can be less than any of about 100 nM, about 50 nM, about 10 nM, about 1 nM, about 500 pM, about 100 pM, or about 50 pM to any of about 2 pM. In some embodiments, the antibody is a human antibody, a humanized antibody, a chimeric antibody, or a single-chain antibody. Binding affinity can be expressed $K_D$ or dissociation constant, and an increased binding affinity corresponds to a decreased $K_D$. One way of determining binding affinity of antibodies to TGFBR3 is by measuring binding affinity of monofunctional Fab fragments of the antibody. To obtain monofunctional Fab fragments, an antibody (for example, IgG) can be cleaved with papain or expressed recombinantly. The affinity of an anti-TGFBR3 Fab fragment of an antibody can be determined by surface plasmon resonance (BIACORE3000™ surface plasmon resonance (SPR) system, BIAcore, INC, Piscaway N.J.). Kinetic association rates ($k_{on}$) and dissociation rates ($k_{off}$) (generally measured at 25° C.) are obtained; and equilibrium dissociation constant ($K_D$) values are calculated as $k_{off}/k_{on}$.

In some embodiments, the antibody binds human TGFBR3, and does not significantly bind a TGFBR3 from another mammalian species. In some embodiments, the antibody binds human TGFBR3 as well as one or more TGFBR3 from another mammalian species. The epitope(s) bound by the antibody can be continuous or discontinuous. In some embodiments, the antibody can bind TGFBR3 and a glycosyl group.

One exemplary anti-TGFBR3 antibody, Anti-RIII-1, is provided herein, which comprises a heavy chain variable ($V_H$) and a light chain variable ($V_L$) region having the following amino acid sequences:

```
Amino Acid Sequence of Anti-RIII-1 V_H:
                                    (SEQ ID NO: 95)
VVESGGGLVK PGGSLKLSCA ASGFTFSDYY MYWVRQTPEK

RLEWVATISD GGSYTYYPDS VKGRFTISRD NAKNNLYLQM

SSLKSEDTAM YYCARDGNYW YFDVWGAGTT VTVSS

Amino Acid Sequence of Anti-RIII-1 V_L:
                                    (SEQ ID NO: 96)
QSVQSPSSLS ASLGGKVTIT CKASQDINKY IAWYQHKPGK

GPRLLIHYTS TLQPGIPSRF SGSGSGRDYS FSISNLEPED

IATYYCLQYD NLRTFGGGTK LEIK
```

The complementary determining regions of the $V_H$ and $V_L$ chains are boldfaced.

In some instances, the anti-TGFBR3 antibody described herein binds the same epitope as Anti-RIII-1 antibody or competes against Anti-RIII-1 from binding to TGFBR3.

A first antibody "binds to the same epitope" as a second antibody if the first antibody binds to the same site on a target compound that the second antibody binds, or binds to a site that overlaps (e.g., 50%, 60%, 70%, 80%, 90%, or 100% overlap, for example, in terms of amino acid sequence or other molecular feature (e.g., glycosyl group, phosphate group, or sulfate group)) with the site that the second antibody binds.

A first antibody "competes for binding" with a second antibody if the binding of the first binding protein to its epitope decreases (e.g., by 10%, 20%, 30%, 40%, 50%, 60%, 70%, 80%, 90%, 100%, or more) the amount of the second binding protein that binds to its epitope. The competition can be direct (e.g., the first antibody binds to an epitope that is the same as, or overlaps with, the epitope bound by the second antibody), or indirect (e.g., the binding of the first antibody to its epitope causes a steric change in the target compound that decreases the ability of the second antibody to bind to its epitope).

In other instances, the anti-TGFBR3 antibody may comprise the same $V_H$ CDRs and/or the same $V_L$ CDRs as Anti-RIII-1 disclosed herein. The regions/residues that are responsible for antigen-binding can be identified from amino acid sequences of the heavy chain/light chain sequences of Anti-RIII-1 (shown above) by methods known in the art. See, e.g., www.bioinf.org.uk/abs; Almagro, J. Mol. Recognit. 17:132-143 (2004); and Chothia et al., J. Mol. Biol. 227:799-817 (1987). A first antibody having the same $V_H$ and/or $V_L$ CDRs as a second antibody means that the first antibody and the second antibody have the same corresponding $V_H$ and/or $V_L$ CDR as determined by the same approach as known in the art.

Determination of CDR regions in an antibody is well within the skill of the art. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Chothia et al. (1989) Nature 342:877; Al-lazikani et al (1997) J. Molec. Biol. 273:927-948)). As used herein, a CDR may refer to CDRs defined by either approach or by a combination of both approaches.

Also within the scope of the present disclosure are functional variants of Anti-RIII-1, which may have essentially the same epitope-binding specificity as Anti-RIII-1 and exhibits at least 20% (e.g., 30%, 40%, 50%, 60%, 70%, 80%, 90%, or greater) of the activity of neutralizing TGFBR3 as relative to Anti-RIII-1.

In some examples, a functional variant of Anti-RIII-1 comprises a $V_H$ chain that includes a $V_H$ CDR1, $V_H$ CDR2, and $V_H$ CDR3 at least 75% (e.g., 80%, 85%, 90%, 95%, or 98%) identical to the corresponding $V_H$ CDRs of Anti-RIII-1, and a $V_L$ chain that includes a $V_L$ CDR1, $V_L$ CDR2, and $V_L$ CDR3 at least 75% (e.g., 80%, 85%, 90%, 95%, or 98%) identical to the corresponding $V_H$ CDRs of Anti-RIII-1. Alternatively, the functional variant of Anti-RIII-1 comprises a $V_H$ chain at least 75% (e.g., 80%, 85%, 90%, 95%, or 98%) identical to the $V_H$ chain (mature or precursor) of Anti-RIII-1 and a $V_L$ chain at least 75% (e.g., 80%, 85%, 90%, 95%, or 98%) identical to the $V_L$ chain (mature of precursor) of Anti-RIII-1.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST® protein searches can be performed with the XBLAST program, score=50, word-length=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST® and Gapped BLAST programs, the default parameters of the respective programs (e.g., XBLAST and NB LAST) can be used.

In some examples, a functional variant of Anti-RIII-1 comprises a $V_H$ chain that includes up to 5 (e.g., 1, 2, 3, 4, or 5) amino acid residue variations in the $V_H$ CDR regions ($V_H$ CDR1, CDR2, and/or CDR3) as compared to the $V_H$ CDRs of Anti-RIII-1, and/or a $V_L$ chain that includes up to 5 (e.g., 1, 2, 3, 4, or 5) amino acid residue variations in the $V_L$ CDR regions ($V_L$ CDR1, CDR2, and/or CDR3) as compared to the $V_H$ CDRs of Anti-RIII-1.

Antibodies capable of inhibiting the TGFBR3-associated signaling pathway as described herein can be made by any method known in the art. See, for example, Harlow and Lane, (1988) Antibodies: A Laboratory Manual, Cold Spring Harbor Laboratory, New York.

In some embodiments, antibodies specific to a target antigen (e.g., human TGFBR3) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, include but are not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-TGFBR3 monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells, of the parent hybridomas that produce monoclonal antibodies capable of interfering with a TGFBR3-associated signaling pathway. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R1N=C=NR, where R and R1 are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting a signaling pathway associated with TGFBR3. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are XENOMOUSE® from Amgen, Inc. (Fremont, Calif.) and HUMAB-MOUSE® and TC MOUSE™ from Medarex, Inc. (Princeton, N.J.). In another alternative, antibodies may be made recombinantly by phage display technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) Proc. Natl. Acad. Sci. USA 81, 6851; Neuberger et al. (1984) Nature 312, 604; and Takeda et al. (1984) Nature 314:452.

Methods for constructing humanized antibodies are also well known in the art. See, e.g., Queen et al., *Proc. Natl. Acad. Sci. USA*, 86:10029-10033 (1989). In one example, variable regions of $V_H$ and $V_L$ of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage scFv library and scFv clones specific to TGFBR3 can be identified from the library following routine procedures. Positive clones can be subjected to further screening to identify those that suppress TGFBR3 activity.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the TGFBR3 polypeptide have been replaced (swapped) with sequences from a closely related, but antigenically distinct protein (such as another member of the neurotrophin protein family). By assessing binding of the antibody to the mutant TGFBR3, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

Other TGFBR3 Inhibitors

TGFBR3 inhibitors other than antibodies capable of interfering with the TGFBR3 signaling pathways as described above can be used in the methods described herein.

In some embodiments of the invention, the TGFBR3 inhibitor comprises at least one antisense nucleic acid molecule capable of blocking or decreasing the expression of a functional TGFBR3. Nucleotide sequences of the TGFBR3 are known in the art. It is routine to prepare antisense oligonucleotide molecules that will specifically bind a target mRNA without cross-reacting with other polynucleotides. Exemplary sites of targeting include, but are not limited to, the initiation codon, the 5' regulatory regions, the coding sequence and the 3' untranslated region. In some embodiments, the oligonucleotides are about 10 to 100 nucleotides in length, about 15 to 50 nucleotides in length, about 18 to 25 nucleotides in length, or more. The oligonucleotides can comprise backbone modifications such as, for example, phosphorothioate linkages, and 2'-O sugar modifications well known in the art.

Alternatively, TGFBR3 expression and/or release can be decreased using gene knockdown, morpholino oligonucleotides, small interfering RNA (siRNA or RNAi), microRNA or ribozymes, methods that are well-known in the art. RNA interference (RNAi) is a process in which a dsRNA directs homologous sequence-specific degradation of messenger RNA. In mammalian cells, RNAi can be triggered by 21-nucleotide duplexes of small interfering RNA (siRNA) without activating the host interferon response. The dsRNA used in the methods disclosed herein can be a siRNA (containing two separate and complementary RNA chains) or a short hairpin RNA (i.e., a RNA chain forming a tight hairpin structure), both of which can be designed based on the sequence of the target gene. Alternatively, it can be a microRNA.

Optionally, a nucleic acid molecule to be used in the method described herein (e.g., an antisense nucleic acid, a small interfering RNA, or a microRNA) as described above contains non-naturally-occurring nucleobases, sugars, or covalent internucleoside linkages (backbones). Such a modified oligonucleotide confers desirable properties such as enhanced cellular uptake, improved affinity to the target nucleic acid, and increased in vivo stability.

In one example, the nucleic acid has a modified backbone, including those that retain a phosphorus atom (see, e.g., U.S. Pat. Nos. 3,687,808; 4,469,863; 5,321,131; 5,399,676; and 5,625,050) and those that do not have a phosphorus atom (see, e.g., U.S. Pat. Nos. 5,034,506; 5,166,315; and 5,792,608). Examples of phosphorus-containing modified backbones include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having 3'-5' linkages, or 2'-5' linkages. Such backbones also include those having inverted polarity, i.e., 3' to 3', 5' to 5' or 2' to 2' linkage. Modified backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In another example, the nucleic acid used in the disclosed methods includes one or more substituted sugar moieties. Such substituted sugar moieties can include one of the following groups at their 2' position: OH; F; O-alkyl, S-alkyl, N-alkyl, O-alkenyl, S-alkenyl, N-alkenyl; O-alkynyl, S-alkynyl, N-alkynyl, and O-alkyl-O-alkyl. In these groups, the alkyl, alkenyl and alkynyl can be substituted or unsubstituted $C_1$ to $C_{10}$ alkyl or $C_2$ to $C_{10}$ alkenyl and alkynyl. They may also include at their 2' position heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide. Preferred substituted sugar moieties include those having 2'-methoxyethoxy, 2'-dimethylaminooxyethoxy, and 2'-dimethylaminoethoxyethoxy. See Martin et al., Helv. Chim. Acta, 1995, 78, 486-504.

In yet another example, the nucleic acid includes one or more modified native nucleobases (i.e., adenine, guanine, thymine, cytosine and uracil). Modified nucleobases include those described in U.S. Pat. No. 3,687,808, The Concise Encyclopedia Of Polymer Science And Engineering, pages 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pages 289-302, CRC Press, 1993. Certain of these nucleobases are particularly useful for increasing the binding affinity of the antisense oligonucleotide to its target nucleic acid. These include 5-substituted pyrimidines, 6-azapyrimidines and N-2, N-6 and O-6 substituted purines (e.g., 2-aminopropyl-adenine, 5-propynyluracil and 5-propynylcytosine). See Sanghvi, et al., eds., Antisense Research and Applications, CRC Press, Boca Raton, 1993, pp. 276-278).

Any of the nucleic acids can be synthesized by methods known in the art. See, e.g., Caruthers et al., 1992, Methods in Enzymology 211, 3-19, Wincott et al., 1995, Nucleic Acids Res. 23, 2677-2684, Wincott et al., 1997, Methods Mol. Bio. 74, 59, Brennan et al., 1998, Biotechnol Bioeng., 61, 33-45, and Brennan, U.S. Pat. No. 6,001,311. It can also be transcribed from an expression vector and isolated using standard techniques.

In other embodiments, the TGFBR3 inhibitor comprises at least one TGFBR3 or TGFBR3 subunit inhibitory compound. As used herein, "TGFBR3 inhibitory compound" or "TGFBR3 subunit inhibitory compound" refers to a compound other than an anti-TGFBR3 that directly or indirectly reduces, inhibits, neutralizes, or abolishes TGFBR3 biological activity. A TGFBR3 inhibitory compound should exhibit any one or more of the following characteristics: (a) binds to TGFBR3 and inhibits its biological activity and/or downstream pathways mediated by TGFBR3 signaling function; (b) prevents, ameliorates, or treats any aspect of cardiac injury; (c) blocks or decreases TGFBR3 receptor activation; (d) increases clearance of TGFBR3; (e) inhibits (reduces) TGFBR3 synthesis, production or release. One skilled in the art can prepare other small molecule inhibitory compounds.

In some embodiments, a TGFBR3 inhibitory compound is a TGFBR3 mutant, which can bind to a TGFBR3 receptor, but cannot elicit signal transduction. Such a mutant may block binding of wild type TGFBR3 to a TGFBR3 receptor thus preventing TGFBR3 signal transduction.

In other embodiments, the TGFBR3 inhibitory compounds described herein are small molecules, which can have a molecular weight of about any of 100 to 20,000 daltons, 500 to 15,000 daltons, or 1000 to 10,000 daltons. Libraries of small molecules are commercially available. The small molecules can be administered using any means known in the art, including inhalation, intraperitoneally, intravenously, intramuscularly, subcutaneously, intrathecally, intraventricularly, orally, enterally, parenterally, intranasally, or dermally. In general, when the TGFBR3-inhibitor according to the invention is a small molecule, it will be administered at the rate of 0.1 to 300 mg/kg of the weight of the patient divided into one to three or more doses. For an adult patient of normal weight, doses ranging from 1 mg to 5 g per dose can be administered.

The above-mentioned small molecules can be obtained from compound libraries. The libraries can be spatially addressable parallel solid phase or solution phase libraries. See, e.g., Zuckermann et al. J. Med. Chem. 37, 2678-2685, 1994; and Lam Anticancer Drug Des. 12:145, 1997. Methods for the synthesis of compound libraries are well known in the art, e.g., DeWitt et al. PNAS USA 90:6909, 1993; Erb et al. PNAS USA 91:11422, 1994; Zuckermann et al. J. Med. Chem. 37:2678, 1994; Cho et al. Science 261:1303, 1993; Carrell et al. Angew Chem. Int. Ed. Engl. 33:2059, 1994; Carell et al. Angew Chem. Int. Ed. Engl. 33:2061, 1994; and Gallop et al. J. Med. Chem. 37:1233, 1994. Libraries of compounds may be presented in solution (e.g., Houghten Biotechniques 13:412-421, 1992), or on beads (Lam Nature 354:82-84, 1991), chips (Fodor Nature 364:555-556, 1993), bacteria (U.S. Pat. No. 5,223,409), spores (U.S. Pat. No. 5,223,409), plasmids (Cull et al. PNAS USA 89:1865-1869, 1992), or phages (Scott and Smith Science 249:386-390, 1990; Devlin Science 249:404-406, 1990; Cwirla et al. PNAS USA 87:6378-6382, 1990; Felici J. Mol. Biol. 222: 301-310, 1991; and U.S. Pat. No. 5,223,409).

In other embodiments, the TGFBR3 inhibitors can be a polypeptide comprising an extracellular portion of a TGFBR3 receptor, wherein the polypeptide specifically binds to a TGFBR3 ligand and blocks its interaction with one or more TGFBR3 receptors. In some embodiments, the extracellular portion of the TGFBR3 receptor is fused to a Fc domain of antibody. Examples of the soluble receptors are described in PCT WO 01/46232.

Identification of TGFBR3 Inhibitors

TGFBR3 inhibitors can be identified or characterized using methods known in the art, whereby reduction, amelioration, or neutralization of a TGFBR3 biological activity is detected and/or measured. For example, an ELISA-type assay may be suitable for qualitative or quantitative measurement of TGFBR3 mediated kinase activation by measuring the phosphorylation of proteins activated through a TGFBR3-associated cascade. The TGFBR3 inhibitors can also be identified by incubating a candidate agent with TGFBR3 and monitoring any one or more of the following characteristics: (a) binding to TGFBR3 and inhibiting its biological activity and/or downstream pathways mediated by TGFBR3 signaling function; (b) preventing, ameliorating, or treating any aspect of cardiac injury; (c) blocking or decreasing TGFBR3 receptor activation; (d) increasing clearance of TGFBR3; (e) inhibiting (reducing) TGFBR3 synthesis, production or release. In some embodiments, a TGFBR3 inhibitor is identified by incubating a candidate agent with TGFBR3 and monitoring binding and attendant reduction or neutralization of a biological activity of TGFBR3. The binding assay may be performed with purified TGFBR3 polypeptide(s), or with cells naturally expressing, or transfected to express, TGFBR3 polypeptide(s). In one embodiment, the binding assay is a competitive binding assay, where the ability of a candidate antibody to compete with a known TGFBR3 inhibitor for TGFBR3 binding is evaluated. The assay may be performed in various formats, including the ELISA format. In other embodiments, a TGFBR3 inhibitor is identified by incubating a candidate agent with TGFBR3 and monitoring attendant inhibition of TGFBR3. Following initial identification, the activity of a candidate TGFBR3 inhibitor can be further confirmed and refined by bioassays, known to test the targeted biological activities. Alternatively, bioassays can be used to screen candidates directly.

The examples provided below provide a number of assays that can be used to screen candidate TGFBR3 inhibitors. Bioassays include but are not limited to flow cytometry of determine competitive binding of TGFBR3 to cells in the presence of candidate TGFBR3 inhibitors; and inhibition of TGFBR3-induced apoptosis in cardiomyocyte cells. In addition, RT-PCR or Real-time PCR which can be used to directly measure TGFBR3 expression or to measure expression of genes upregulated by TGFBR3.

(B) Let-7 Enhancers MicroRNAs are small noncoding RNAs which are originally transcribed by RNA polymerase II and are proceed by two endonuclease systems to form mature single strand RNA (Ha et al., *Nat Rev Mol Cell Biol* 15, 509-524 (2014)). A RISC (RNA-induced silencing) complex guides miRNA to the 3'-UTR of mRNAs, by sequence complementarity, leading to inhibition of protein translation, mRNA degradation and deadenylation (Meister et al., *Nat Rev Genet* 14, 447-459 (2013)).

Let-7 is an evolutionarily conserved microRNA. It is enriched and ubiquitously expressed in all mammalian tissues (Roush et al., *Trends Cell Biol* 18, 505-516 (2008)). MicroRNA let-7 is crucial for heart development (Rustagi et al., *PLoS One* 10, e0139359 (2015); Cao et al., *Int J Mol Med* 30, 1095-1104 (2012)) and cardiomyocyte maturation (Kuppusamy et al., *Proc Natl Acad Sci USA* 112, E2785-2794 (2015)). Although let-7 is one of the early discovered microRNA and is abundant and conserved from *C. elegans* to mammals (Roush et al., *Trends Cell Biol* 18, 505-516 (2008)), little is known about the function of let-7 in myocardial infarction. As examples, the nucleotide sequences of human precursor let-7a and let-7f are provided below (SEQ ID NOs:89-93) with the mature region italicized (SEQ ID NO:94):

hsa-let-7a-1
(SEQ ID NO: 89)
UGGGA*UGAGGUAGUAGGUUGUAUAGUUUUAGGGU*CACACCCACCACUGG

GAGAUAACUAUACAAUCUACUGUCUUUCCUA hsa-let-7a-2
(SEQ ID NO: 90)
AGGU*UGAGGUAGUAGGUUGUAUAGUUUAGAAUUA*CAUCAAGGGAGAUAA

CUGUACAGCCUCCUAGCUUUCCU hsa-let-7a-3
(SEQ ID NO: 91)
GGGU*GAGGUAGUAGGUUGUAUAGUUU*GGGGCUCUGCCCUGCUAUGGGAU

AACUAUACAAUCUACUGUCUUUCCU hsa-let-7f-1
(SEQ ID NO: 92)
UCAGAG*UGAGGUAGUAGAUUGUAUAGUUGUGGGG*UAGUGAUUUUACCCU

GUUCAGGAGAUAACUAUACAAUCUAUUGCCUUCCCUGA hsa-let-7f-2
(SEQ ID NO: 93)
UGUGGGA*UGAGGUAGUAGAUUGUAUAGUUUUAGGGU*CAUACCCCAUCUU

GGAGAUAACUAUACAGUCUACUGUCUUUCCCACG

The let-7 enhancer to be used in the methods described herein is a molecule that improves, activates, or increases (including significantly) the biological activity of an endogenous let-7 microRNA (including any isoform of let-7, for example, let-7a or let-7f). The term "enhancer" implies no specific mechanism of biological action whatsoever, and is deemed to expressly include and encompass all possible pharmacological, physiological, and biochemical interactions with an endogenous let-7 or a downstream gene whether direct or indirect. For the purpose of the present disclosure, it will be explicitly understood that the term "enhancer" encompasses all of the previously identified terms, titles, and functional states and characteristics whereby the let-7 itself (e.g., human let-7) is substantially improved, activated, or increased in any meaningful degree, e.g., by at least 20%, 50%, 70%, 85%, 90%, 100%, 150%, 200%, 300%, or 500%, or by 10-fold, 20-fold, 50-fold, 100-fold, 1000-fold, or $10^4$-fold.

In some embodiments, a let-7 enhancer for use in the methods described herein is a let-7 nucleic acid, which refers to any nucleic acid having similar biological activity as a native microRNA let-7, for example, let-7a or let-7f. Such a let-7 nucleic acid may comprise the nucleotide sequence of the mature sequence of a let-7 microRNA (SEQ ID NO:94). Alternatively, a let-7 nucleic acid can be a precursor let-7 molecule, which can be processed to generate a functional, mature microRNA to inhibit the expression of its downstream gene(s). In some embodiments, the let-7 nucleic acid contains one or more modified nucleotides, for example, as described herein.

In other embodiments, a let-7 enhancer for use in the methods described herein can be an LIN28 inhibitor. LIN28 is a family of RNA-binging proteins that may promote pluripotency via regulation of the microRNA let-7. LIN28 proteins may repress let-7 maturation by binding the let-7 precursor and derepression of let-7 targets. Example LIN28 proteins include LIN28A (a.k.a., CSDD1, LIN-28, LIN28, ZCCHC1, lin-28A, or lin-28 homolog A), and LIN28B (a.k.a. CSDD2, or Lin-28.2). The human LIN28 proteins are provided under Genbank Accession No.: NC_000001.11 (LIN28A) and Genbank Accession No.: NC_000006.12 (LIN28B). LINAny LIN28 inhibitors can be used in the methods described herein as a let-7 enhancer. An LIN28 inhibitor may be an anti-LIN28 antibody that inhibits the activity of LIN28. Alternatively, an LIN28 inhibitor may be a small interfering RNA (siRNA or RNAi) or an antisense RNA that target the LIN28 gene and/or mRNA and thus block its transcription/translation (e.g., via RNA interference). In other examples, the LIN28 inhibitors can be small molecules that inhibit the activity of the protein, for example, N-methyl-N-[3-(3-methyl[1,2,4]triazolo[4,3-b]pyridazin-6-yl)phenyl]acetamide (Roos et al., A Small-Molecule Inhibitor of Lin28. *ACS Chem Biol.* 2016 Aug. 22), and Aurothioglucose hydrate. Such small molecule inhibitors may be obtained by screening a combinatory compound library via routine practice.

Any of the nucleic acid-based let-7 enhancers may contain non-naturally-occurring nucleobases, sugars, or covalent internucleoside linkages (backbones). Such a modified oligonucleotide confers desirable properties such as enhanced cellular uptake, improved affinity to the target nucleic acid, and increased in vivo stability.

In one example, the nucleic acid-based let-7 enhancer may have a modified backbone, including those that retain a phosphorus atom (see, e.g., U.S. Pat. Nos. 3,687,808; 4,469,863; 5,321,131; 5,399,676; and 5,625,050) and those that do not have a phosphorus atom (see, e.g., U.S. Pat. Nos. 5,034,506; 5,166,315; and 5,792,608). Examples of phosphorus-containing modified backbones include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having 3'-5' linkages, or 2'-5' linkages. Such backbones also include those having inverted polarity, i.e., 3' to 3', 5' to 5' or 2' to 2' linkage. Modified backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In another example, the nucleic acid-based let-7 enhancer used in the disclosed methods may include one or more substituted sugar moieties. Such substituted sugar moieties can include one of the following groups at their 2' position: OH; F; O-alkyl, S-alkyl, N-alkyl, O-alkenyl, S-alkenyl, N-alkenyl; O-alkynyl, S-alkynyl, N-alkynyl, and O-alkyl-O-alkyl. In these groups, the alkyl, alkenyl and alkynyl can be substituted or unsubstituted $C_1$ to $C_{10}$ alkyl or $C_2$ to $C_{10}$ alkenyl and alkynyl. They may also include at their 2' position heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide. Preferred substituted sugar moieties include those having 2'-methoxyethoxy, 2'-dimethylaminooxyethoxy, and 2'-dimethylaminoethoxyethoxy. See Martin et al., Helv. Chim. Acta, 1995, 78, 486-504.

In yet another example, the nucleic acid-based let-7 enhancer may include one or more modified native nucleobases (i.e., adenine, guanine, thymine, cytosine and uracil). Modified nucleobases include those described in U.S. Pat. No. 3,687,808, The Concise Encyclopedia Of Polymer Science And Engineering, pages 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pages 289-302, CRC Press, 1993. Certain nucleobases mentioned above are particularly useful for increasing the binding affinity of the antisense oligonucleotide to its target nucleic acid. These include 5-substituted pyrimidines, 6-azapyrimidines and N-2, N-6 and O-6 substituted purines (e.g., 2-aminopropyl-adenine, 5-propynyluracil and 5-propynylcytosine). See Sanghvi, et al., eds., Antisense Research and Applications, CRC Press, Boca Raton, 1993, pp. 276-278).

Any of the let-7 enhancers described herein can be synthesized by methods known in the art. See, e.g., Caruthers et al., 1992, Methods in Enzymology 211, 3-19, Wincott et al., 1995, Nucleic Acids Res. 23, 2677-2684, Wincott et al., 1997, Methods Mol. Bio. 74, 59, Brennan et al., 1998, Biotechnol Bioeng., 61, 33-45, and Brennan, U.S. Pat. No. 6,001,311. It can also be transcribed from an expression vector and isolated using standard techniques.

(C) Pharmaceutical Compositions

One or more of the TGFBR3 inhibitors (e.g. antibodies), and/or one or more of the let-7 enhancers as described herein can be mixed with a pharmaceutically acceptable carrier (excipient) to form a pharmaceutical composition for use in treating a target disease, injury or condition. In some embodiments, the composition is used for treatment of cardiac injury. In some embodiments, both the TGFBR3 inhibitors and let-7 enhancers or PEG conjugates thereof as described herein can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. See, e.g., Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In some examples, the pharmaceutical composition described herein comprises liposomes containing the anti-TGFBR3 antibodies, which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The anti-TGFBR3 antibodies as described herein, and/or the let-7 enhancer as also described herein may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the anti-TGFBR3 antibodies, which matrices are in the form of shaped articles, e.g. films, or microcapsules. Examples of sustained-release matrices include polyesters, hydrogels (for example, poly(2-hydroxyethyl-methacrylate), or poly(v nylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

The pharmaceutical compositions to be used for in vivo administration must be sterile. This is readily accomplished by, for example, filtration through sterile filtration membranes. Therapeutic anti-TGFBR3 antibodies compositions may be placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., TWEEN™ 20, 40, 60, 80 or 85) and other sorbitans (e.g., SPAN™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as INTRALIPID™, LIPO-SYN™, INFONUTROL™, LIPOFUNDIN™ and LIPIPH-YSAN™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 .im, particularly 0.1 and 0.5. im, and have a pH in the range of 5.5 to 8.0.

The emulsion compositions can be those prepared by mixing an anti-TGFBR3 or a let-7 enhancer with INTRA-LIPID™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

(D) Treatment of Cardiac Injuries

Cardiac injuries include, but are not limited to, cardiac acute coronary syndrome, myocardial infarction (including MI and other non-MI acute heart injuries caused by coronary diseases), myocarditis, cardiomyopathy, and post-operation cardio-protection. A "cardiac injury" is defined as induced cardiomyocyte death (e.g., apoptosis). In some embodiments, cardiomyocyte death can be induced by cardiomyocyte cell apoptosis through p38 MAPK pathway activation. In other embodiments, cardiomyocyte death can be induced by a stressor. Stressors of cardiac injury include, but are not limited to trauma, toxins, clot formations, plaque, oxygen deprivation, nutrient deprivation.

Two large coronary arteries and their branches supply the blood supply to the myocardium. Coronary occlusion, occlusion of one or more of these blood vessels, is one of the major causes of myocardial infarction. In some embodiments, the occlusion may result from the formation of a clot that develops suddenly when an atheromatous plaque ruptures through the sublayers of a blood vessel. In other embodiments, the narrow, roughened inner lining of a sclerosed artery leads to complete thrombosis. Other causes of MI may be attributed to a sudden increased unmet need for blood supply to the heart, as in shock, hemorrhage, and severe physical exertion, and to restriction of blood flow through the aorta, (e.g. aortic stenosis).

Any of the anti-TGFBR3 antibodies, or let-7 enhancers as described herein can be used to ameliorate a cardiac injury, such as those described herein. To practice the method disclosed herein, an effective amount of the pharmaceutical composition described herein that contains anti-TGFBR3 antibodies or a let-7 enhancer can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the anti-TGFBR3 antibody-containing or let-7 enhancer-containing composition as described herein can be aerosolized using a fluorocarbon formulation and a metered dose inhaler, or inhaled as a lyophilized and milled powder.

As used herein, "an effective amount" refers to the amount of each active agent required to confer therapeutic effect on the subject, either alone or in combination with one or more other active agents. In some embodiments, the therapeutic effect is reduced cardiac injury and/or increased immune activity. Determination of whether an amount of the anti-TGFBR3 antibody or the let-7 enhancer achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a target disease/disorder. Alternatively, sustained continuous release formulations of an anti-TGFBR3 antibody or let-7 enhancer may be appropriate. Various formulations and devices for achieving sustained release are known in the art.

In one example, dosages for an anti-TGFBR3 antibody or let-7 enhancer as described herein may be determined empirically in individuals who have been given one or more administration(s) of the anti-TGFBR3 antibody or let-7 enhancer. Individuals are given incremental dosages of the antagonist. To assess efficacy of the antagonist, an indicator of the disease/disorder can be followed.

Generally, for administration of any of the anti-TGFBR3 antibodies or let-7 enhancers described herein, an initial candidate dosage can be about 2 mg/kg. For the purpose of the present disclosure, a typical daily dosage might range from about any of 0.1 μg/kg to 3 μg/kg to 30 μg/kg to 300 μg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering an initial dose of about 2 mg/kg, followed by a weekly maintenance dose of about 1 mg/kg of the anti-TGFBR3 antibody or let-7 enhancer, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 μg/mg to about 2 mg/kg (such as about 3 μg/mg, about 10 μg/mg, about 30 μg/mg, about 100 μg/mg, about 300 μg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. In some embodiments, an ELISA assay is used. The dosing regimen (including the anti-TGFBR3 antibody(s) or let-7 enhancer(s)) can vary over time.

In some embodiments, for an adult patient of normal weight, doses ranging from about 0.3 to 5.00 mg/kg may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of an anti-TGFBR3 antibody or let-7 enhancer as described herein will depend on the specific anti-TGFBR3 antibody/Let-7 enhancer, the type and severity of the disease/disorder, whether the anti-TGFBR3 antibody/Let-7 is administered for preventive or therapeutic purposes, previous therapy, the patient's clinical history and response to the antagonist, and the discretion of the attending physician. A clinician may administer an anti-TGFBR3 antibody/Let-7 enhancer, until a dosage is reached that achieves the desired result. In some embodiments, the desired result is a decrease in cardiac injury and/or increased immune activity. Methods of determining whether a dosage resulted in the desired result would be evident to one of skill in the art. Administration of one or more anti-TGFBR3 antibodies or let-7 enhancers can be continuous or intermittent, depending, for example, upon the recipient's physiological condition, whether the purpose of the administration is therapeutic or prophylactic, and other factors known to skilled practitioners. The administration of an anti-TGFBR3 antibody may be essentially continuous over a preselected period of time or may be in a series of spaced dose, e.g., either before, during, or after developing a target disease or disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

In some embodiments, the anti-TGFBR3 antibodies or the let-7 enhancer described herein are administered to a subject in need of the treatment at an amount sufficient to reduce cardiomyocyte death, by at least 5% (e.g., 10%, 20%, 30%, 40%, 50%, 60%, 70%, 80%, 90% or greater) in vivo. In other embodiments, the anti-TGFBR3 antibodies or let-7 enhancers are administered in an amount effective in reducing the activity level of TGFBR3 or enhance the activity of let-7 by at least 5% (e.g., 10%, 20%, 30%, 40%, 50%, 60%, 70%, 80%, 90% or greater).

Conventional methods, known to those of ordinary skill in the art of medicine, can be used to administer the pharmaceutical composition to the subject, depending upon the type of disease/injury to be treated or the site of the disease/injury. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In some embodiments, the pharmaceutical composition is injected locally. In some embodiments, the local injection is intramyocardial injection or intracoronary injection. In addition, it can be administered to the subject via injectable depot routes of administration such as using 1-, 3-, or 6-month depot injectable or biodegradable materials and methods. In some examples, the pharmaceutical composition is administered intraocularlly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble anti-TGFBR3 antibodies can be administered by the drip method, whereby a pharmaceutical formulation containing the anti-TGFBR3 antibodies and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the anti-TGFBR3 antibodies, can be dissolved and administered in a pharmaceutical excipient such as Water-for-Injection, 0.9% saline, or 5% glucose solution.

In one embodiment, an anti-TGFBR3 antibody or let-7 enhancer is administered via site-specific or targeted local delivery techniques. Examples of site-specific or targeted local delivery techniques include various implantable depot sources of the anti-TGFBR3 antibodies/Let-7 enhancer or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338.

Therapeutic compositions containing a polynucleotide (e.g., the nucleic acid-based TGFBR3 inhibitors or nucleic acid-based let-7 enhancers) are administered in a range of about 100 ng to about 200 mg of DNA for local administration in a gene therapy protocol. In some embodiments, concentration ranges of about 500 ng to about 50 mg, about 1 μg to about 2 mg, about 5 μg to about 500μg, and about 20 μg to about 100 μg of DNA or more can also be used during a gene therapy protocol.

The subject to be treated by the methods described herein can be a mammal, such as a farm animals, sport animals, pets, primates, horses, dogs, cats, mice and rats. In one example, the subject is a human. The anti-TGFBR3 antibody-containing or let-7 enhancer-containing composition may be used for protecting cardiomyocyte death caused by various factors. In some examples, the subject may be a human patient having, suspected of having, or at risk for cardiac injury, such as cardiac acute coronary syndrome, myocardial infarction (including MI and other non-MI acute heart injuries caused by coronary diseases), myocarditis, cardiomyopathy, and post-operation cardio-protection. Such a patient can also be identified by routine medical practices.

A subject having a target disease or disorder (e.g., cardiovascular disease) can be identified by routine medical examination, e.g., laboratory tests, organ functional tests, CT scans, or ultrasounds. A subject suspected of having any of such target disease/disorder might show one or more symptoms of the disease/disorder. A subject at risk for the disease/disorder can be a subject having one or more of the risk factors associated with that disease/disorder. Such a subject can also be identified by routine medical practices.

The particular dosage regimen, i.e., dose, timing and repetition, used in the method described herein will depend on the particular subject (e.g., a human patient) and that subject's medical history.

In some embodiments, the anti-TGFBR3 antibody or let-7 enhancer may be co-used with another suitable therapy for cardiac injury, such as those described herein. Alternatively or in addition, the anti-TGFBR3 antibody or let-7 enhancer may also be used in conjunction with other agents that serve to enhance and/or complement the effectiveness of the agents.

Treatment efficacy for a target disease/disorder can be assessed by, e.g., a method described in the Examples below.

II. Kits for Use in Alleviating a Target Disease

The present disclosure also provides kits for use in ameliorating a cardiac injury. Such kits can include one or more containers comprising a TGFBR3 inhibitor (e.g., an antibody that binds TGFBR3, e.g., any of those described herein) or a let-7 enhancer such as a let-7 nucleic acid.

In some embodiments, the kit can comprise instructions for use in accordance with any of the methods described herein. The included instructions can comprise a description of administration of the aptamer to treat, delay the onset, or alleviate a target disease as those described herein. The kit may further comprise a description of selecting an individual suitable for treatment based on identifying whether that individual has the target disease. In still other embodiments, the instructions comprise a description of administering the aptamer to an individual at risk of the target disease.

The instructions relating to the use of a TGFBR3 inhibitor or a let-7 enhancer generally include information as to dosage, dosing schedule, and route of administration for the intended treatment. The containers may be unit doses, bulk packages (e.g., multi-dose packages) or subunit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a disease or injury associated with cardiac injury, such as those described herein. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a TGFBR3 inhibitor and/or let-7 enhancer as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

III. Assays for Measuring TGFBR3 and/or Let-7

Also provided herein are assay methods for measuring the level of TGFBR3, the level of let-7, or both in a biological sample. Such a method may comprise: (i) providing a biological sample suspected of containing TGFBR3, let-7, or both, (ii) contacting the biological sample with an agent (e.g., an antibody) that binds a cleaved form of TGFBR3 (for example, SEQ ID NO: 3), an agent that binds let-7, or both, (iii) measuring the level of the cleaved form of TGFBR3, let-7, or both, in the biological sample; and (iv) determining presence or absence of TGFBR3, let-7, or both in the biological sample. Any conventional methods, such as ELISA, hybridization, or PCR may be used for measuring the level of TGFBR3, the level of let-7, or both in a biological sample.

A suitable biological sample can be obtained from a subject as described herein via routine practice. Non-limiting examples of biological samples include fluid samples such as blood (e.g., whole blood, plasma, serum), urine, and saliva, and solid samples such as tissue (e.g., skin, lung, nasal) and feces. Such samples may be collecting using any method known in the art or described herein, e.g., buccal swab, nasal swab, venipuncture, biopsy, urine collection, or stool collection. In particular examples, the biological sample for use in the assay methods described herein are plasma samples or serum samples.

The agent such as antibody for use in measuring TGFBR3 may specifically bind to the cleaved form (soluble form) of the receptor. In some examples, such an antibody does not bind to membrane-bound TGFBR3. The antibody for use in the assay methods may specifically bind to the cleaved form of TGFBR3 that is glycosylated. For example, the antibody may bind to an N-terminal epitope that is glycosylated.

Agents for measuring let-7 may be a nucleic acid molecule (DNA or RNA) comprising a nucleotide sequence complementary to let-7 or a portion thereof. "Complementary," as used herein, refers to the nucleobase complementarity commonly known in the art. For example, adenine is complementary to thymine (in DNA) or uracil in RNA; and guanine is complementary to cytosine. "Sequence complementarity", or "nucleic acid sequences being complementary to one another", as used herein, means when the two nucleic acid molecules are aligned antiparallel to each other, the nucleotide bases at each position, or at most positions in the sequences are complementary, and that the two nucleic acid molecules can hybridize and form a duplex under suitable conditions, e.g., hybridization temperature. As known in the art, a sequence complementarity needs not be 100% for the two nucleic acid molecules to hybridize and form a duplex. The sequence complementarity between the capture probe (or the detecting probe described herein) and the target nucleic acid may be at least 80% complementary to the corresponding region in the target nucleic acid. In some embodiments, the capture probe contains a fragment that is at least 80% (e.g., 85%, 90%, 95%, 98%, or 100%) complementary to the first segment of the target nucleic acid. In some instances, the capture probe contains a fragment that is completely complementary (100% complementary) to the first segment of the target nucleic acid. Such a capture probe may be used in differentiating the target nucleic acid from substantially similar nucleic acids, for example, nucleic acids having 1, 2, or 3 base differences relative to the target nucleic acid.

The nucleic acid-based agent for measuring let-7 may contain up to 100 nucleotides (e.g., up to 80 nt, 60 nt, 50 nt, or 30 nt). In some embodiments, the nucleic acid may be 8-50 nucleotides in length, e.g., 8-40, 8-30, 10-30, 15-30, or 15-20 nucleotides in length. In other examples, the nucleic acid may contain a linker (e.g., a poly A or poly T linker) for attaching to a support member (see details below). Alternatively or in addition, the nucleic acid may be conjugated with a labeling agent, directly or via a linker.

The agent for measuring let-7 as described herein can be immobilized on a support member via a conventional method. As used herein, "immobilized" means attached, bound, or affixed, covalently or non-covalently, so as to prevent dissociation or loss of the capture probe, but does not require absolute immobility with respect to either the capture probe or the support member. A support member can be a solid or semi-solid member with a surface that can be used to specifically attach, bind or otherwise capture a nucleotide probe (e.g., the capture probe of the present disclosure), such that the nucleotide probe becomes immobilized with respect to the support member. The agent for measuring let-7 may be conjugated with a labeling agent. "Conjugated", as used herein, means the labeling agent is attached to the detecting probe, covalently or non-covalently. The labeling agent can be any molecule, particle, or the like, that facilitates detection, directly or indirectly, using a suitable detection technique. In the case of direct detection, the labeling agent may be a molecule or moiety capable of releasing a signal that can be directly interrogated and/or detected (e.g., a fluorescent label or a dye). In a first non-limiting case of indirect detection, the labeling agent may be a molecule or moiety capable of converting a substrate (e.g., an enzyme) to a product that is capable of releasing a detectable signal. For example, the labeling agent may be a luciferase, which converts luciferin to oxyluciferin to emit detectable lights. In another non-limiting case of indirect detection, the labeling agent is a binding ligand to a molecule or moiety capable of converting a substrate (e.g., an enzyme), wherein the converted substrate releases detectable signals.

The antibody binding to the cleaved form of TGFBR3 or the agent for measuring let-7 may be incubated with a biological sample as described herein under suitable conditions for a suitable period to allow for the binding of the cleaved form of TGFBR3 to the antibody, or let-7 to the agent. Such bindings can then be detected via routine technology.

The presence and/or amount of TGFBR3 and/or let-7 in the biological sample determined by any of the assay methods described herein would have various clinical and non-clinical applications.

As disclosed herein, let-7 (for example, let-7a and let-7f) was found to be downregulated in samples from patients having MI. Further, TGFBR3, a microRNA let-7 target gene, was found to be upregulated 24 hours post myocardial infarction in injured heart tissue. Because TGFBR3 can be cleaved and released into extracellular matrix, plasma TGFBR3 thus could be used as a biomarker for assessing MI and other cardiac injuries. A reduced level of let-7 and/or an increased level of plasma TGFBR3 can be indicators of cardiac injury.

Unlike Troponin, there is a basal expression level of TGFBR3 in plasma. According to the pig experiment in Example 1, the concentration of plasma TGFBR3 was relatively consistent in each individual pig. A standard concentration range for diagnosis can therefore be established.

The level of soluble TGFBR3, the level of let-7, or both in a biological sample obtained from a subject (e.g., a human patient) as described herein may be relied on to determine whether the subject has or at risk for a cardiac injury, e.g., MI. In some examples, the TGFBR3/Let-7 level may be compared with a pre-determined value as described herein. An elevated level of TGFBR3 and/or a reduced level of let-7 in the biological sample as compared with the pre-determined value indicate that the subject has or is at risk for a cardiac injury.

As used herein, "an elevated level of TGFBR3" means that the level of TGFBR3 is above a pre-determined value, such as a pre-determined threshold or a control level of TGFBR3. Control levels are described in detail herein. An elevated level of TGFBR3 includes a TGFBR3 level that is, for example, 1%, 5%, 10%, 20%, 30%, 40%, 50%, 60%, 70%, 80%, 90%, 100%, 150%, 200%, 300%, 400%, 500% or more above a pre-determined value. An elevated level of TGFBR3 also includes increasing a phenomenon from a zero state (e.g., no or undetectable TGFBR3 in a control) to a non-zero state (e.g., some TGFBR3 or detectable TGFBR3 in a sample).

As used herein, "a decreased level of let-7" means that the level of let-7 is below a pre-determined value, such as a pre-determined threshold or a control level of let-7. A decreased level of let-7 includes a let-7 level that is, for example, 1%, 5%, 10%, 20%, 30%, 40%, 50%, 60%, 70%, 80%, 90%, 100%, 150%, 200%, 300%, 400%, 500% or more below a pre-determined value. A decreased level of let-7 also includes decreasing a phenomenon from a non-zero state (e.g., some Let level or detectable let-7 in a sample) to a zero state (e.g., no or undetectable let-7 in a control).

A pre-determined value can be the TGFBR3 or let-7 level in a control sample (a controlled level), which can be measured using any of the methods known in the art or described herein. In some examples, the pre-determined value is measured by the same method applied for measuring the TGFBR3 or let-7 level in a biological sample. The control level may be a level of the TGFBR3 or let-7 in a control sample, control subject, or a population of control subjects.

The control may be (or may be derived from) a normal subject (or normal subjects). Normal subjects, as used herein, refer to subjects that are apparently healthy and show no signs or symptoms of cardiac injury. The population of control subjects may therefore be a population of normal subjects.

It is to be understood that the methods provided herein do not require that a control level be measured every time a subject is tested. Rather, in some embodiments, it is contemplated that control levels are obtained and recorded and that any test level is compared to such a pre-determined level. The pre-determined level may be a single-cutoff value or a range of values.

By comparing the TGFBR3 and/or let-7 level(s) of a biological sample obtained from a subject and the pre-determined value as described herein, the subject can be identified as having or at risk for a cardiac injury.

General Techniques

The practice of the present invention will employ, unless otherwise indicated, conventional techniques of molecular biology (including recombinant techniques), microbiology, cell biology, biochemistry and immunology, which are within the skill of the art. Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Several animal models have been utilized to mimic human MI, which is a leading cause of mortality and heart failure worldwide. To investigate the underlying mechanisms or to explore the potential therapeutic strategy of MI, small animal models are often used because of the cost, genomic manipulating techniques and the ease of handling. However, the heart rates, contractile protein expression, metabolism et al. of small animals are much different from those of a human (Zaragoza et al., *J Biomed Biotechnol* 2011, 497841 (2011)), which makes it difficult to directly translate small animal studies to human clinic. Unlike small laboratory animals, porcine provides an ideal animal model for human coronary artery diseases because its cardiovascular anatomy and the progression of diseases are similar to those in humans (Munz et al., *Comp Med* 61, 445-452 (2011)). Therefore, the porcine MI model is advantageous to reveal functions of small non-coding RNA in the early phase of MI.

Among such, porcine is considered one of the most representative models. In this study, a porcine MI model and next-generation sequencing techniques were applied to discover differential microRNA expression occurring in early MI. The aim for this study was to identify miRNAs response to early myocardial infarction using the porcine MI model. The pig heart tissues from myocardial infarction were collected. RNA was subjected to next-generation sequencing (NGS). The differential expression level was confirmed by real-time qPCR and the potential target genes were identified by screening. The function of miRNAs and the target genes were studied by gain of function and loss of function approaches. Further, to extend these finding to potential clinical applications, plasma samples were collected from experimental pigs and clinical patients for further investigation.

It was found that microRNAs let-7a and let-7f were enriched in heart tissues and show significant downregulation within 24 hours post-MI. Their downstream target genes TGFBR3 and HMGA2 were upregulated correlatively. Inhibition of let-7 by Tough Decoy (TuD) RNA enhanced cardiomyocyte apoptosis under stress. Overexpression of TGFBR3 activated p38 MAPK and led to cardiomyocyte apoptosis. Inhibition of p38 MAPK rescued TGFBR3 induced activation of Caspase 3. These data suggest that downregulation of let-7 (including let-7a and let-7f) would promote cardiomyocyte death through the TGFBR3 and p38 MAPK signaling pathways. In support of this, overexpression of let-7 or inhibition of TGFBR3 reduced p38 MAPK activity and rescued cell death induced by serum starvation. Finally, it was confirmed that the plasma level of let7 is significantly reduced in patients with acute MI (n=25) compared with that in normal control (n=9; $P>0.05$). This study identifies differential expression of microRNAs in early MI, uncovers the roles of let-7 and TGFBR3 in cardiovascular diseases, and also provides potential biomarkers and therapeutic targets for cardiac injuries such as MI. The microRNA let-7/TGFBR3 axis induces cardiomyocyte cell death in early myocardial infarction and both plasma let-7 and TGFBR3 respond to heart injury.

Materials and Methods (i) LAD Ligation in Porcine Model

Surgical anesthesia was introduced in about 22 Kg Lanyu minipigs by use of Zoletil (12.5 mg/kg; Virbac, France), Rompun (0.2 ml/kg; Bayer Healthcare, Germany), and atropine (0.05 mg/kg; TBC, Taiwan) before intubation. They were attached to a respirator for intermittent positive pressure ventilation with a mixture of oxygen, air, and Isoflurane (1.5 to 2%; Baxter Healthcare, Guayama, PR). For the sustained administration of saline or anesthetic, a venous indwelling catheter was maintained in an ear vein during surgery. After surgery, an antibiotic (Ampolin, YSP) to prevent infection and an analgesic to alleviate pain (Keto, YSP) were given. MI surgery was performed by permanent occlusion at the midleft anterior descending artery.

(ii) Total RNA and Plasma miRNA Extraction

Trizol reagent (Invitrogen) was used to extract total RNA from tissues and cells. Pig plasma was prepared from the peripheral blood through centrifugation. Then, small RNA was extracted from 200 μl of plasma by mirVana PARIS kit (Ambion) following the manufacturer's instructions. Five feto-moles of synthetic microRNA, cel-mir-39, was added into the samples as an internal control for normalization of technical variations.

(iii) miRNA Profiling with Next Generation Sequencing (NGS)

RNA samples from pig infarct and remote tissues were collected from 1, 2 and 4 hour post MI. The small RNA libraries were prepared following TRUSEQ® Small RNA (Illumina) instruction and sequenced according to protocols of Illumina for HiSeq 2000 platform. The generated raw fastq data was analyzed using miRSeq (Pan et al., *Biomed Res Int* 2014, 462135 (2014)) to examine the overall sequencing qualities and derive the miRNA expression profiles.

(iv) miRNA Stem-Loop Real-Time PCR

Fifty ng of total RNA were subjected to reverse transcription using Taqman microRNA reverse transcription kit (Applied Biosystems) with synthesized oligonucleotides which form stem loop structure and antisense of microRNA as RT primer. Quantitative PCR was performed using a universal primer, which recognizes the stem-loop sequence, and a microRNA specific primer in OmicsGreen qPCR Master Mix (Omics Bio) with an ABI 7500 real-time PCR system (Applied Biosystems). RT primers, universal primer and microRNA specific primer were listed in Table 2. Quantitative PCR was also performed using TaqMan microRNA detection system. Stem loop RT primers and detection probes for each microRNAs were provided by TaqMan. The quantitative PCR procedure was carried out following manufacturer's instructions provided with the Taqman microRNA assays (Applied Biosystems) using universal PCR master mix (Applied Biosystems).

TABLE 1

Stem-loop qPCR primer list

| microRNA | RT-primer | SEQ ID NO: | Forward Primer | SEQ ID NO: | Universal reward Primer |
| --- | --- | --- | --- | --- | --- |
| Let-7a/f | CTCAACTGGTGTCGTG GAGTCGGCAATTCAGT TGAGAACTATAC | 4 | ACACTCCAGCTGGTGAGG TAGT AG(A/G)TTGT | 9 | CTGGTGTCGTGGAGTCGGCAATTC (SEQ ID NO: 88) |
| miR-22 | CTCAACTGGTGTCGTG GAGTCGGCAATTCAGT TGAGACAGTTCT | 5 | ACACTCCAGCTGGGAAGC TGCCA | 10 | |
| miR-101 | CTCAACTGGTGTCGTG GAGTCGGCAATTCAGT TGAGTTCAGTTA | 6 | ACACTCCAGCTGGGTACA GTACT GTGATA | 11 | |
| miR-103 | CTCAACTGGTGTCGTG GAGTCGGCAATTCAGT TGAGTCATAGCC | 7 | ACACTCCAGCTGGGAGCA GCATT GTACAGGG | 12 | |
| miR-199-3p | CTCAACTGGTGTCGTG GAGTCGGCAATTCAGT TGAGTAACCAAT | 8 | ACACTCCAGCTGGGACAG TAGTC TGCACAT | 13 | |

(v) Real-Time PCR

Total RNA was reverse transcribed using SuperScript III (Invitrogen). Quantitative real-time PCR was performed using OmicsGreen qPCR Master Mix (Omics Bio) with an ABI 7500 real-time PCR system (Applied Biosystems). Primers used are listed in Table 3.

TABLE 2 qPCR-primers

| Name | Forward | SEQ ID NO: | Reverse | SEQ ID NO: |
|---|---|---|---|---|
| Rat_Aak1 | GTTTGCCCCCATAGCACTCT | 14 | CCTAGAGTGCCCACCTTGTG | 49 |
| Rat_Akap6 | TGGACTCCTCCTAAAGCCGA | 15 | CGTGTCCTTCAGTCCTGCTT | 50 |
| Rat_Btg2 | GGTATGAGCCACGGGAAGAG | 16 | TAATGATCGGTCAGTGCGTCC | 51 |
| Rat_Bzw1 | CAAGCTCGCCATGTTGACTG | 17 | AGCTGCTGAAACCCCTTCTTT | 52 |
| Rat_Cap1 | GGGGGAGATGTGCAGAAACA | 18 | GTTTATTACCGGCTGGCTGC | 53 |
| Rat_Cpeb3 | ATGGCTCTCAGCCTTTGGAC | 19 | AGTTCAACAGCTCGAAGGGG | 54 |
| Rat_Ddi2 | GGGGAGTTACCAGAGTGTGC | 20 | CTTCTGACGCTCTGCATCCT | 55 |
| Rat_Dusp1 | CCTCCAAGGAGGATATGAAGCG | 21 | AGAGAGGGGTGCTACAGGAG | 56 |
| Rat_Dusp16 | TCCTCAACAAGGAGCTGATGC | 22 | GCACTCGCAGGAAGTGAGAT | 57 |
| Rat_Eif2c1 | ACTGTGGGCAAACCGATCAA | 23 | CCACCTCCCGGTTGACTCT | 58 |
| Rat_Hmga2 | AGAGACCCAGAGGAAGACCC | 24 | TTGTTGTGGCCATTTCCTGG | 59 |
| Rat_Klh124 | TTTCGAGGATGTGTCCCAGC | 25 | GCGCATGACTGCCTCAAAAA | 60 |
| Rat_Map3k1 | TGGCGCCTGAGGTACTAAGA | 26 | CGGGATGGATGGTGCAGTAG | 61 |
| Rat_Map4k3 | GGTCTGTGTTGGCGTCAGTA | 27 | GCGGGTATCTGACTCTGTG | 62 |
| Rat_Mapk6 | AAAGCGAGAGCCTCGGAAAC | 28 | ATACAACGGGACTTCTCCGAC | 63 |
| Rat_Mef2c | AGGGAATGGATACGGCAACC | 29 | ACATCCTCAGACACTGATGGC | 64 |
| Rat_Nphp3 | AGGCAGTCTGTACGGGTTTG | 30 | GGCTTGTCCTTGCCTAAGGT | 65 |
| Rat_Nras | TGGCACTCAAGGCTGTATGG | 31 | GGGCATCAGTGAGGCTTGAA | 66 |
| Rat_Pdpk1 | TCTTCGTCCACACGCCTAAC | 32 | ACTGCTCTGGTACTGTTGCC | 67 |
| Rat_Ppara | CGGCGTTGAAAACAAGGAGG | 33 | CCTTGGCAAATTCCGTGAGC | 68 |
| Rat_Ppargc1a | GGGACGAATACCGCAGAGAG | 34 | CGGCGCTCTTCAATTGCTTT | 69 |
| Rat_Ppargc1b | GACTGGATGAAGGCGACACA | 35 | TCTGCAGCAGTGAAAGCTCA | 70 |
| Rat_Prkaa2 | GTGGTGACCCTCAAGACCAG | 36 | CCATGAAGGAACCCGTTGGA | 71 |
| Rat_Sh2b3 | GAGAGCCAAGCACCTCCG | 37 | ATATCCACCACCGAGGGGAA | 72 |
| Rat_Taok1 | GCGTTTGGATGAAGCACAGG | 38 | ACCCTTTGTTCCAGCTCTCG | 73 |
| Rat_Tgfbr1 | TCCAAACCACAGAGTAGGCAC | 39 | TGGATTCCGCCAATGGAACA | 74 |
| Rat_TGFBR3 | AGACATTCACCAAGCCCCTG | 40 | CGCTCCGATCACAAATGCTG | 75 |
| Rat_Tmem65 | GGACTTGGCCTTGCAGGTTA | 41 | CCAACAGCCTTGCCCAAATG | 76 |
| Rat_Trappc1 | GGCAATTCCGATGACTGTCC | 42 | GGGATCCCTGCTTGCTTCTT | 77 |
| Rat_Trib2 | CTTCGAGCGGAGCTATGGAG | 43 | GCTTGACACGAGTCCTCTCT | 78 |
| Pig_HMGA2 | CCTACCTCCCAATCTCCCGA | 44 | GTCCTCTCTTCTGAGGCACC | 79 |
| Pig_TGFBR1 | TGACCTAATTCCGCGAGACA | 45 | GCCAGATGGTGGCTTTCCTG | 80 |
| Pig_TGFBR3 | GAGTACCTCCAGCCCAAACC | 46 | CCTGGAAAGCACTGTAGGGG | 81 |
| Pig_Pri-Let-7a/f | CAGACAGCATCATCCAAGCATC | 47 | TAAAAGTATCCCCACCCAACCTG | 82 |
| Pig_LIN28A | TTCTGCATTGGGAGCGAGAG | 48 | GCAGTTTGCATTCCTTGGCA | 83 |

(vi) Isolation of Rat Neonatal Cardiomyocytes

Rat neonatal cardiomyocyte isolation was described previously. Hearts were removed from neonatal rats (P1-P3) and placed in cold HBSS/PBS (1:1) buffer to wash away blood. Ventricles were then minced and subjected into 1 mg/ml of trypsin (Sigma) for pre-digestion at 4° C. for 4 hours. Trypsin was removed after pre-digestion and 0.8 mg/ml of collagenase type II (Worthington) was added to digest the remaining tissues at 37° C. for 15 mins. After digestion, serum containing medium was used to neutralize enzyme activity and cells were then passed through a 40-um cell strainer. Enzyme was removed by centrifugation at 1200 rpm for 5 mins. Cell pellet was resuspend in plating medium (DMEM-low glucose with 10% FBS). Fibroblasts were removed by pre-plating cells for 1 hour in incubator. Suspension cells were then plated in 1% gelatin-coated plate. After myocytes were attached, cells were maintained in culture medium (DMEM-low glucose with 1% FBS) for further experiments.

(vii) Lentivirus-Mediated Let-7 Overexpression, Inhibition and TGFBR3 Knockdown

Let-7a and let-7f genome sequences were amplified by forward primer: 5'-CCAAAAGGCCTGGTCCTAGA (SEQ ID NO:84) and reverse primer: 5'-CCA AAAGGCCTGGTCCTAGA (SEQ ID NO:85). shRNAs of rat TGFBR3 were designed to target CTGTAGACAAA GACTCTTTC (SEQ ID NO:86; shTGFBR3-2) and CAT TGCATTTGCAGCATTTG (SEQ ID NO:87; shTGFBR3-3). Scramble shRNA and shTGFBR3 sequences were inserted into pLKO_TRC014, using AgeI and EcoRI. Lentivirus carrying let-7 Tough Decoy RNA was purchased from Sigma.

Figure 6:
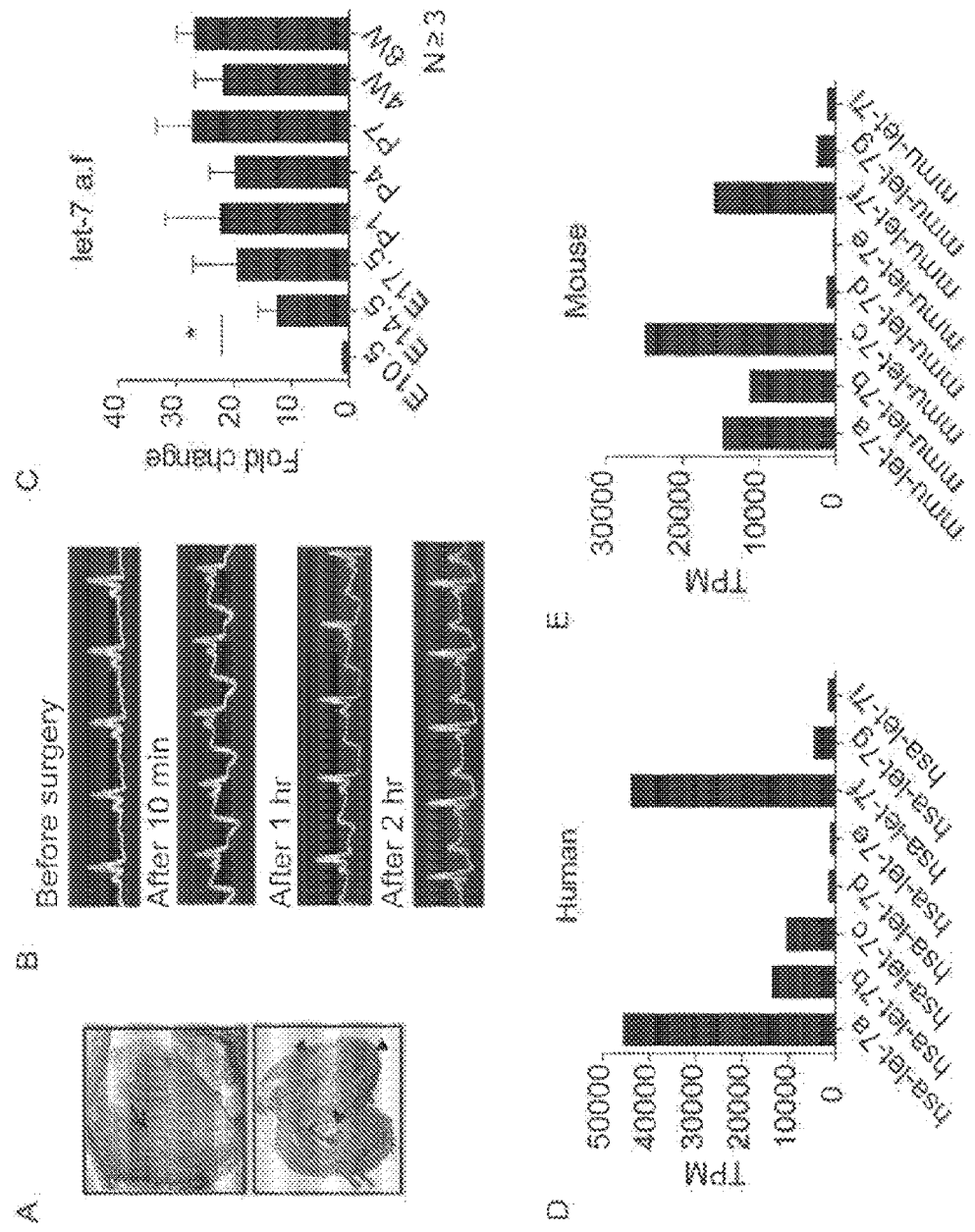
FIG. 6 shows miRNA let-7 expression during heart development and the abundance of let-7 families in human and mouse hearts. Panel A: Pig LAD (left anterior descending) artery ligation surgery. The arrow points out the ligation site and the arrow heads indicate the infarct area after ligation. Panel B: Electrocardiogram (EKG) measurement to evaluate the surgery. Panel C: Let-7a.f expression during mouse heart development by stem-loop qPCR. Bars and error bars indicate mean and SEM (n≥3). Panels D-E: Expression of let-7 family in human and mouse hearts according to NGS databases from Meunier et al, *Genome Res* 23, 34-45 (2013).

Results (i) Let-7a and Let-7f Respond to Myocardial Infarction within 24-Hour Post MI in Porcine Model To discover microRNA expression change in early myocardial infarction, pigs were subjected to LAD (left anterior descending) artery ligation for 1, 2, 4 and 24 hours. To minimize the individual difference, in addition to infarct tissue, remote tissues were collected as internal control. Samples from 1, 2, 4 hour post MI were used for NGS analysis (FIG. 1, Panel A). LAD ligation site and infarct area are indicated in FIG. 6 Panel A. To confirm the success of surgery, electrocardiography (ECG) was used (FIG. 6 Panel B) and Tunel assay was performed (FIG. 1 Panel B). Heart enriched microRNAs were selected as shown in Table 3 below. According to their abundance and differential expression level, microRNA let-7a, let-7f, miR-22, miR-101, miR-103 and miR-199a-3p were chosen for validation using stem-loop qPCR analysis. All of these miRNAs presented a trend of downregulation in 4-hr post MI and reached a significant downregulation in 24 hr post MI (FIG. 1 Panels C-G). miR-22 is a regulator of cardiac remodeling under stress. Overexpression of miR-22 leads to cardiac hypertrophy and miR-22 deficient mice display cardiac dilation and fibrosis (Huang et al., *Circ Res* 112, 1234-1243 (2013); and Gurha et al., *Circulation* 125, 2751-2761 (2012)). miR-101 plays a role in anti-fibrosis post myocardial infarction (Pan et al., *Circulation* 126, 840-850 (2012)). Recently, miR-103 has been reported to mediate programmed necrosis of cardiomyocytes (Wang et al., *Circ Res* 117, 352-363 (2015)). miR-199a regulates cardiac metabolism and autophagy (el Azzouzi et al., *Cell Metab* 18, 341-354 (2013); Li et al., *Cell Death Differ*, (2015)). Among these microRNAs, let-7a and let-7f are highly abundant and remarkably decreased in one-day post-MI. To further confirm this result, specific TaqMan probes were used to detect the expression level of let-7a and let-7f. Using both let-7a and let-7f specific probes validated the significant downregulation in 24 hours-post MI (FIG. 1 Panel H).

TABLE 3

| | Small RNA sequencing (transcripts per million (TPM) > 1000) | | | | | |
|---|---|---|---|---|---|---|
| miR_ID | 1 h_Infarct | 1 h_Remote | 2 h_Infarct | 2 h_Remote | 4 h_Infarct | 4 h_Remote |
| ssc-Let-7a | 30172.2 | 27851.2 | 35146.2 | 35587.2 | 29144.2 | 39063.2 |
| ssc-Let-7c | 7663.1 | 4854.1 | 9455.1 | 9097.1 | 8620.1 | 9385.1 |
| ssc-Let-7f | 13471.2 | 18265.2 | 26652.2 | 41751.2 | 33089.2 | 37037.2 |
| ssc-Let-7g | 2519.1 | 2908.1 | 3850.1 | 3917.1 | 2811.1 | 3208.1 |
| ssc-Let-7i | 715.1 | 875.1 | 1173.1 | 1105.1 | 636.1 | 689.1 |
| ssc-miR-1 | 601294.1 | 583743.1 | 584500.1 | 578140.1 | 557386.1 | 549868.1 |
| ssc-miR-100 | 7688.1 | 6124.1 | 5241.1 | 5312.1 | 4771.1 | 4021.1 |
| ssc-miR-101 | 10792.2 | 19996.2 | 10251.2 | 14862.2 | 11282.2 | 12086.2 |
| ssc-miR-103 | 1137.2 | 1410.2 | 1512.2 | 1432.2 | 1235.2 | 2665.2 |
| ssc-miR-125b | 1362.2 | 1487.2 | 1290.2 | 1192.2 | 2029.2 | 1994.2 |
| ssc-miR-126-3p | 7914.1 | 9780.1 | 9626.1 | 5740.1 | 7895.1 | 8998.1 |
| ssc-miR-133a-3p | 1308.2 | 1272.2 | 710.2 | 1214.2 | 1046.2 | 1238.2 |
| ssc-miR-140-3p | 1611.1 | 2349.1 | 2337.1 | 2025.1 | 1478.1 | 1544.1 |
| ssc-miR-143-3p | 39063.1 | 45670.1 | 73564.1 | 69426.1 | 50463.1 | 44539.1 |
| ssc-miR-148a-3p | 1561.1 | 3196.1 | 3474.1 | 2619.1 | 1294.1 | 2124.1 |
| ssc-miR-151-3p | 801.1 | 1516.1 | 2083.1 | 1290.1 | 1360.1 | 1062.1 |
| ssc-miR-152 | 961.1 | 985.1 | 1586.1 | 1193.1 | 1262.1 | 1133.1 |
| ssc-miR-181a | 2432.2 | 3218.2 | 1804.2 | 1872.2 | 1817.2 | 2364.2 |
| ssc-miR-186 | 1001.1 | 1072.1 | 581.1 | 583.1 | 910.1 | 1050.1 |
| ssc-miR-199a-3p | 1368.2 | 2008.2 | 1036.2 | 2406.2 | 1880.2 | 1991.2 |
| ssc-miR-199b-3p | 683.1 | 1003.1 | 515.1 | 1201.1 | 939.1 | 994.1 |
| ssc-miR-21 | 3182.1 | 4530.1 | 5208.1 | 4448.1 | 4335.1 | 3084.1 |
| ssc-miR-22-3p | 1120.1 | 940.1 | 418.1 | 481.1 | 637.1 | 1366.1 |
| ssc-miR-24-3p | 10177.2 | 10779.2 | 6328.2 | 4830.2 | 17021.2 | 12584.2 |
| ssc-miR-26a | 1253.1 | 1163.1 | 1782.1 | 1551.1 | 898.1 | 1211.1 |
| ssc-miR-27a | 830.1 | 693.1 | 1652.1 | 1488.1 | 1160.1 | 1088.1 |
| ssc-miR-27b-3p | 5057.1 | 9843.1 | 9416.1 | 6523.1 | 7687.1 | 8895.1 |
| ssc-miR-30a-3p | 701.1 | 742.1 | 1017.1 | 663.1 | 614.1 | 834.1 |
| ssc-miR-30a-5p | 14770.1 | 6050.1 | 9268.1 | 9978.1 | 5986.1 | 6907.1 |
| ssc-miR-30d | 8406.1 | 7049.1 | 4040.1 | 4499.1 | 3968.1 | 6000.1 |
| ssc-miR-30e-3p | 1194.1 | 2374.1 | 2735.1 | 3125.1 | 2044.1 | 1351.1 |
| ssc-miR-30e-5p | 8099.1 | 7356.1 | 10233.1 | 9361.1 | 9990.1 | 9732.1 |
| ssc-miR-378 | 189172.2 | 189110.2 | 152510.2 | 151394.2 | 206826.2 | 199199.2 |
| ssc-miR-486 | 2666.2 | 936.2 | 972.2 | 2220.2 | 1426.2 | 1380.2 |
| ssc-miR-99a | 1207.1 | 824.1 | 531.1 | 733.1 | 829.1 | 1034.1 |
| ssc-miR-99b | 1459.1 | 1147.1 | 1046.1 | 1195.1 | 1194.1 | 1296.1 |

According to the NGS results obtained in this study, let-7a and let-7f are the most abundant let-7 members in pig heart tissues (FIG. 1 Panel I). In humans, the most abundant let-7 members are also let-7a and let-7f (FIG. 6 Panel D) and in mouse, that are let-7a, let-7b, let-7c and let-7f (FIG. 6 Panel E) (Meunier et al., Genome Res 23, 34-45 (2013)). The expression of let-7a/f in heart is correlated to heart development in mouse model (FIG. 6C), which implies that let-7 has an important role in heart development.

To examine whether the downregulation of let-7 was due to the upregulation of let-7 in the remote area, the expression level of let-7a and let-7f in infarct and remote area were further compared. The significant downregulation of let-7a and let-7f was only found in the infarct area but not in the remote zone of pig hearts (FIG. 1 Panel J). Similar results were detected in mouse MI model. let-7a was significantly downregulated in one-day and two-day post MI and gradually increased in 6-day post MI (FIG. 1 Panel K).

Figure 2:
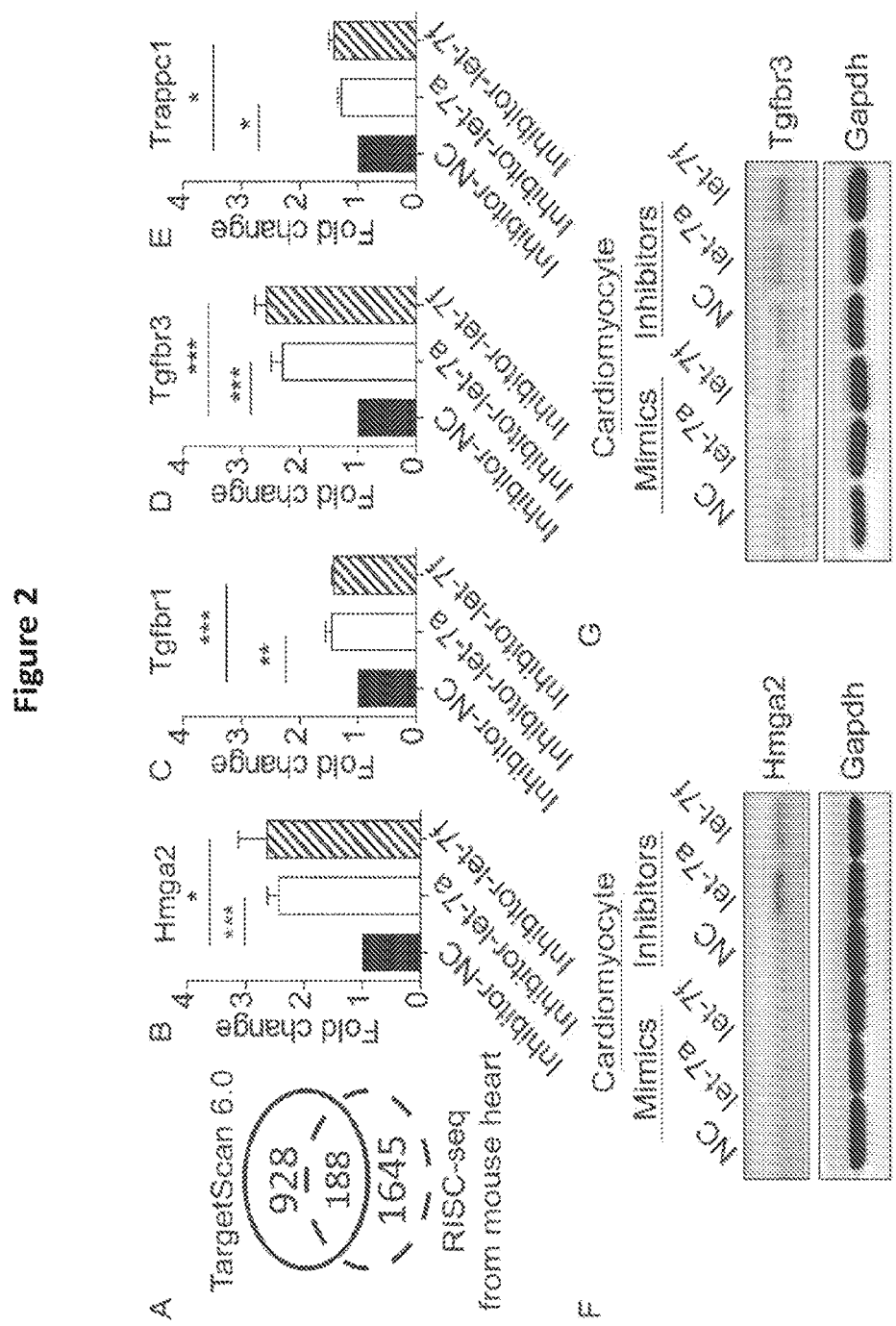
FIG. 2 shows the identification of let-7 target genes. Panel A: Strategy of target gene identification. Twenty-nine genes were selected from 188 genes which were both identified in the heart RISC-seq database and predicted by TargetScan 6.0. Panels B-E: Potential target gene expression after transfection of let-7a and let-7f inhibitors in rat neonatal cardiomyocytes. Bars and error bars indicate mean and SEM from more than three independent experiments. Panels F-G: Western blot of Hmga2 and Tgfbr3 expression in rat neonatal cardiomyocytes transfected with let-7a and let-7f inhibitors. Panels H-J: HMGA2, TGFBR1 and TGFBR3 RNA expression levels in hearts of porcine 24 h post MI. Panel K: Expression level of primary let-7a.f transcript in hearts of porcine 24 h post MI. Panel L: Expression level of LIN28A in hearts of porcine 24 h post MI. An I/R ratio indicates RNA expression level in the infarct area to that in the remote area. Panel M: Western blot of TGFBR3, TGFBR1 and HMGA2 in pig infarct and remote tissues. Panel N: Immunochemistry staining of HMGA2 and TGFBR3 in pig infarct tissue. Panel O: Immunofluorescence staining of TGFBR3 and cardiac troponin T in pig infarct heart tissue 24 hours post MI. TGFBR3 was expressed in cardiomyocytes.
Figure 2:
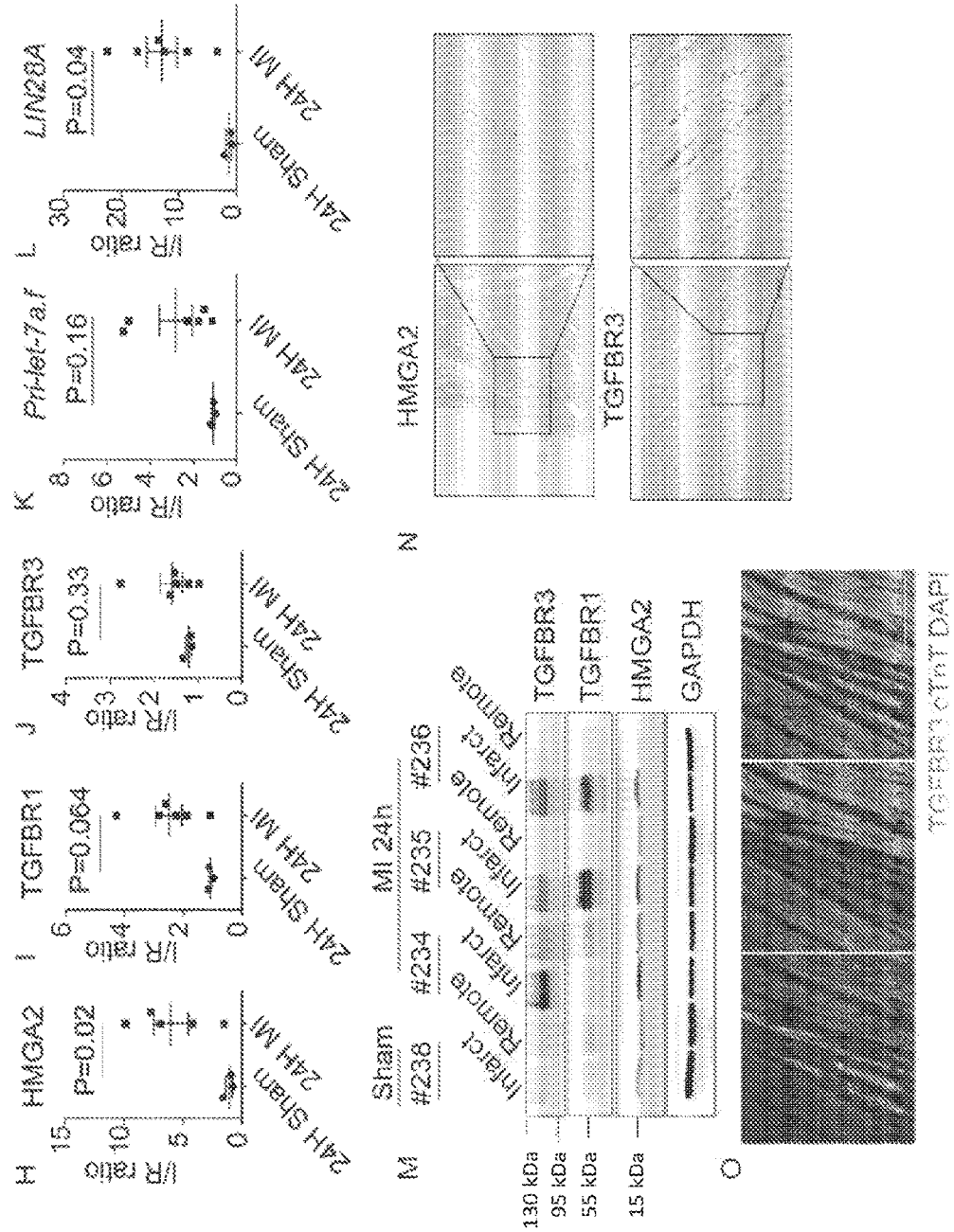
Figure 7:
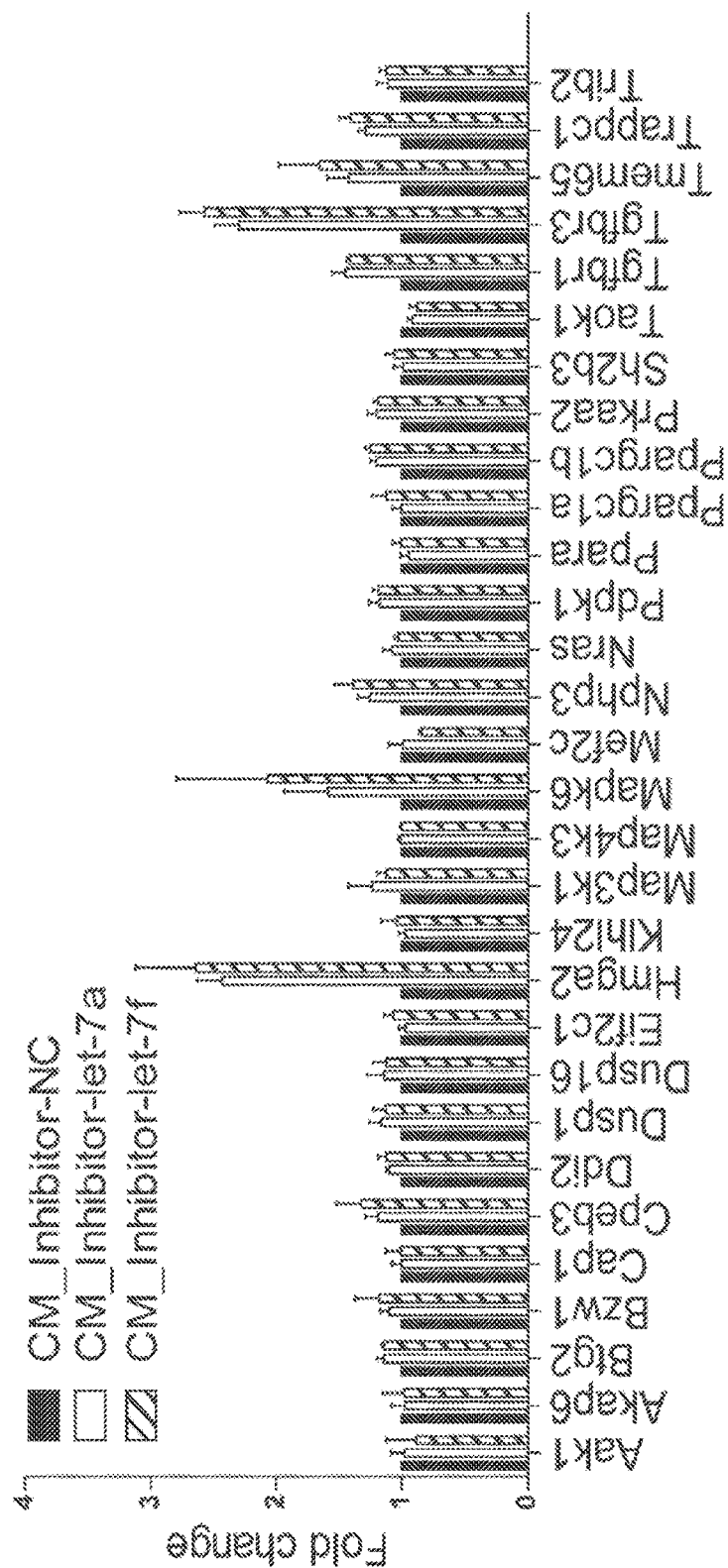
FIG. 7 shows screening of let-7a and let-7f target genes. Twenty-nine genes were selected according to heart RISC (RNA-induced silencing complex)-sequencing and TargetScan. Hmga2 is considered as a positive control. Let-7a and let-7f inhibitors were transiently transfected into rat neonatal cardiomyocytes. RNA was collected one day after transfection. The bars and error bars indicate mean and SEM from more than three independent experiments.

(ii) Hmga2, Tgfbr1, TGFBR3 and Trappc1 are Potential Targets of Let-7 in Cardiomyocytes MicroRNA let-7 is enriched in both cardiomyocytes and non-cardiomyocytes (Seeger et al., J Mol Cell Cardiol 94, 145-152 (2016)). To identify the target genes of let-7, a heart RISC-seq database (Matkovich et al., Circ Res 108, 18-26 (2011)) and TargetScan software (Shin et al., Mol Cell 38, 789-802 (2010)) were compared (FIG. 2 Panel A). Twenty-nine candidates and Hmga2, as a positive control, were chosen for further validation in cardiomyocytes (FIG. 7). After transfection of let-7a and let-7f inhibitors into rat neonatal cardiomyocytes, several potential target genes were upregulated, including Hmga2, Tgfbr1, TGFBR3 and Trappc1 (FIG. 2 Panels B-E and FIG. 7). Hmga2 is a well-known target of let-7 (Mayr et al., Science 315, 1576-1579 (2007); Copley et al., Nat Cell Biol 15, 916-925 (2013)). Tgfbr1 and TGFBR3 were also confirmed respectively as targets of let-7 (Tzur et al., PLoS One 4, e7511 (2009); Tay et al., Cell Res 24, 259-260 (2014)). The protein expression levels of Hmga2 and TGFBR3 in cardiomyocytes were also confirmed (FIG. 2 Panels F and G).

In the pig MI model, HMGA2 was significantly upregulated (FIG. 2 Panel H). Though there were minor increase in TGFBR1 and TGFBR3 (FIG. 2 Panels I and J), the protein expression level of HMGA2, TGFBR1 and TGFBR3 were upregulated in the pig infarct tissues (FIG. 2 Panel M). To explore the possible upstream regulator of let-7, primary let-7 transcript and LIN28 expression was also evaluated. LIN28 is a RNA binding protein repressing let-7 maturation during development and diseases (Thornton et al., Trends Cell Biol 22, 474-482 (2012)) and in involved in several biological processes (Zhu et al., Cell 147, 81-94 (2011); Iliopoulos et al., Cell 139, 693-706 (2009)). The result showed that primary let-7 transcript was not decreased (FIG. 2 Panel K) but LIN28A was increased in the infarct area (FIG. 2 Panel L). These results indicate the downregulation of let-7 in the infarct area may be due to the repression by LIN28, but not the reduction of transcription.

Further, immunochemistry was performed to confirm the expression of HMGA2 and TGFBR3 in pig infarct tissues. The expression of HMGA2 was be found in the boundary of necrotic tissue and healthy tissue and TGFBR3 was found in cardiomyocytes which are surrounded by immune cells (FIG. 2 Panels N and O). These data support the hypothesis that the repression of let-7 induced expression of Hmga2 and TGFBR3 in the infarct areas, which may play a role in the progression of ischemic injury.

Figure 3:
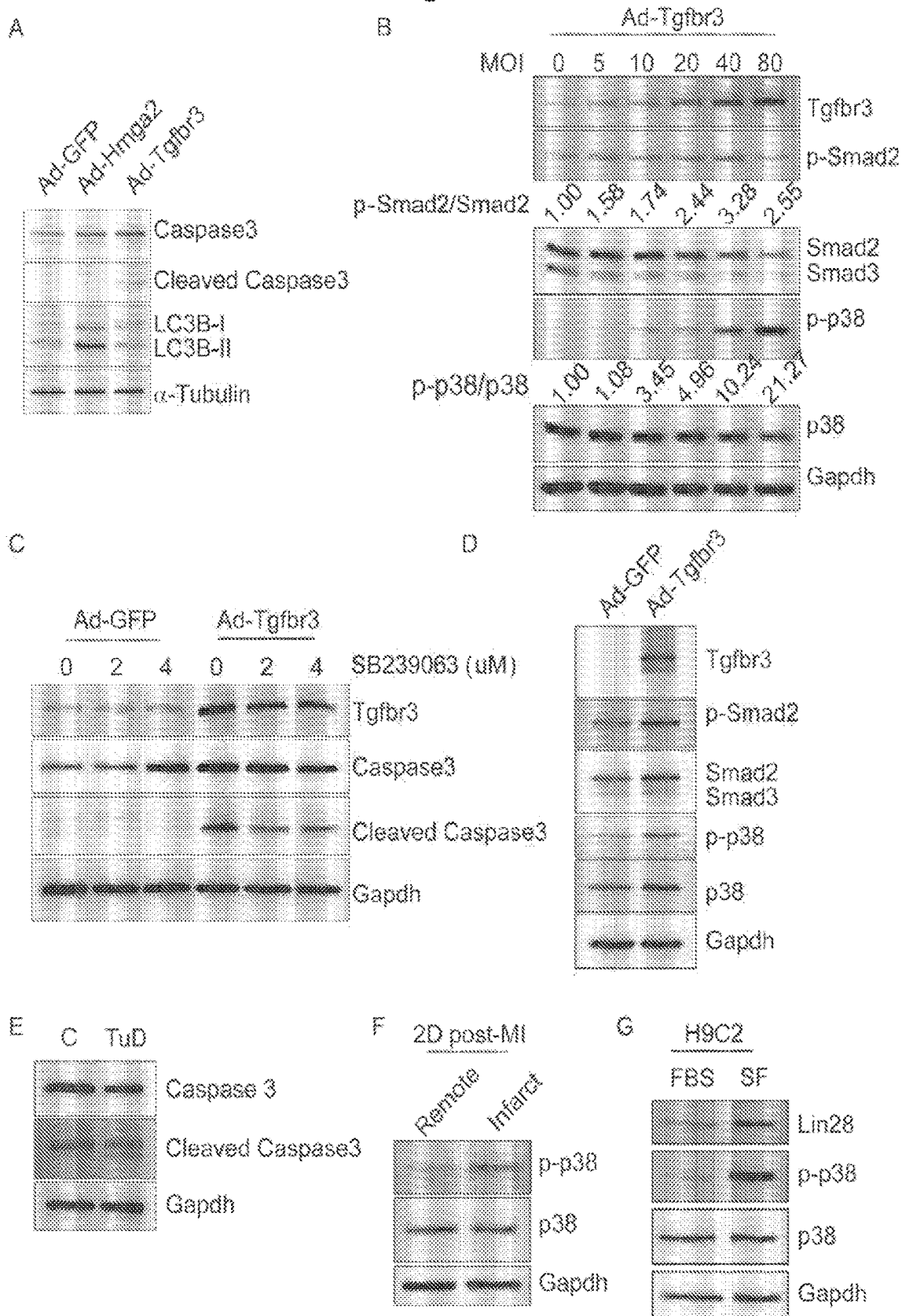
FIG. 3 shows that Tgfbr3 induce cardiomyocytes apoptosis through p38 MAPK. Panel A: Adenoviruses mediated Hmga2 and Tgfbr3 expression in rat neonatal cardiomyocytes. Cells were collected one day after infection. Cleaved LC3B is an autophagy marker and cleaved caspase3 indicates apoptosis. Panel B: Activation of Smad2 and p38 MAPK signaling in a dose dependent Tgfbr3 expression. MOI: multiplicity of infection. Panel C: The treatment of p38 MAPK inhibitor SB239063 partially rescued Tgfbr3 induced cell apoptosis in rat neonatal cardiomyocytes. Cells were infected by adenoviruses for one day and SB239063 was then added into culture medium for another one day. Panel D: Adenoviruses carrying GFP and Tgfbr3 were intramyocardially injected into mouse heart for two days. Protein was extracted from the heart tissue. Tgfbr3 overexpression induced activation of p38 MAPK. Panel E: Inhibition of let-7 by lentiviruses mediated Tough Decoy (TuD) RNA expression in rat neonatal cardiomyocyte enhanced serum and glucose depletion induced apoptosis. Cells were infected by lentiviruses and selected by puromycin for one week. After recovery for four days, serum and glucose were removed from the culture medium for one day. Cells were collected one day after serum and glucose depletion. Panel F: Myocardial infarction activated p38 MAPK activity. Protein was extracted from remote and infarct tissue from mouse heart 2-day after MI. Panel G: Serum depletion induced p38 MAPK activation in H9C2 cell line.

(iii) TGFBR3 Activates Noncanonical TGF/3 Signaling-p38 MAPK and Enhanced Cardiomyocytes Apoptosis To further understand the underlying mechanisms of let-7 in myocardial infarction, Hmga2 and TGFBR3 overexpressing adenoviruses were generated. Interestingly, overexpression of Hmga2 induced cleavage of LC3B, an autophagy marker (FIG. 3 Panel A) and overexpression of TGFBR3 induced cleavage of Caspase 3, an apoptosis marker (FIG. 3 Panel A). TGFBR3, also named betaglycan, is a co-receptor of TGFβ superfamily. It has multiple functions in different tissues (Bilandzic et al., Mol Cell Endocrinol 339, 180-189; 2011). To investigate the downstream signaling of TGFBR3 in cardiomyocytes, rat neonatal cardiomyocytes were infected with TGFBR3 overexpressing adenoviruses with different infection units (MOI). The canonical and noncanonical TGFβ signaling was examined. The result showed an obvious dose-dependent activation of p38 MAPK in cardiomyocytes (FIG. 3 Panel B), which may explain how apoptosis occurs after TGFBR3 overexpression in cardiomyocytes. Treatment of p38 MAPK inhibitor SB239063 partially rescued TGFBR3 induced apoptosis in cardiomyocytes (FIG. 3 Panel C). In vivo, an activation of p38 MAPK was also found in mouse heart infected with TGFBR3 overexpressing adenoviruses for 2 days (FIG. 3 Panel D). To inhibit let-7 in rat neonatal cardiomyocytes, Tough Decoy (TuD) RNA was expressed by lentiviruses. TuD RNA was sufficient to inhibit both let-7a and let-7f expression and induced upregulation of TGFBR3 (FIG. 8 Panels A-C). Inhibition of let-7 by TuD RNA enhanced cardiomyocyte apoptosis 24 h after depletion of glucose and serum (FIG. 3 Panel E). Activation of p38 MAPK has an impact on cardiac remodeling and cardiomyocytes apoptosis (Ren et al., J Mol Cell Cardiol 38, 617-623 (2005)). The activation of p38 MAPK was also detected in the mouse infarct tissue of 2-day post MI (FIG. 3 Panel F) and serum-free induced H9C2 rat embryonic cell line (FIG. 3 Panel G). The results indicate that let-7/TGFBR3 axis is involved in cardiomyocytes apoptosis, which may through the activation of p38 MAPK. It is expected that, in addition to the TGFBR3 inhibitors or let-7 enhancers disclosed herein, p38 MAPK inhibitors may also be used for alleviating cardiac injury.

Figure 4:
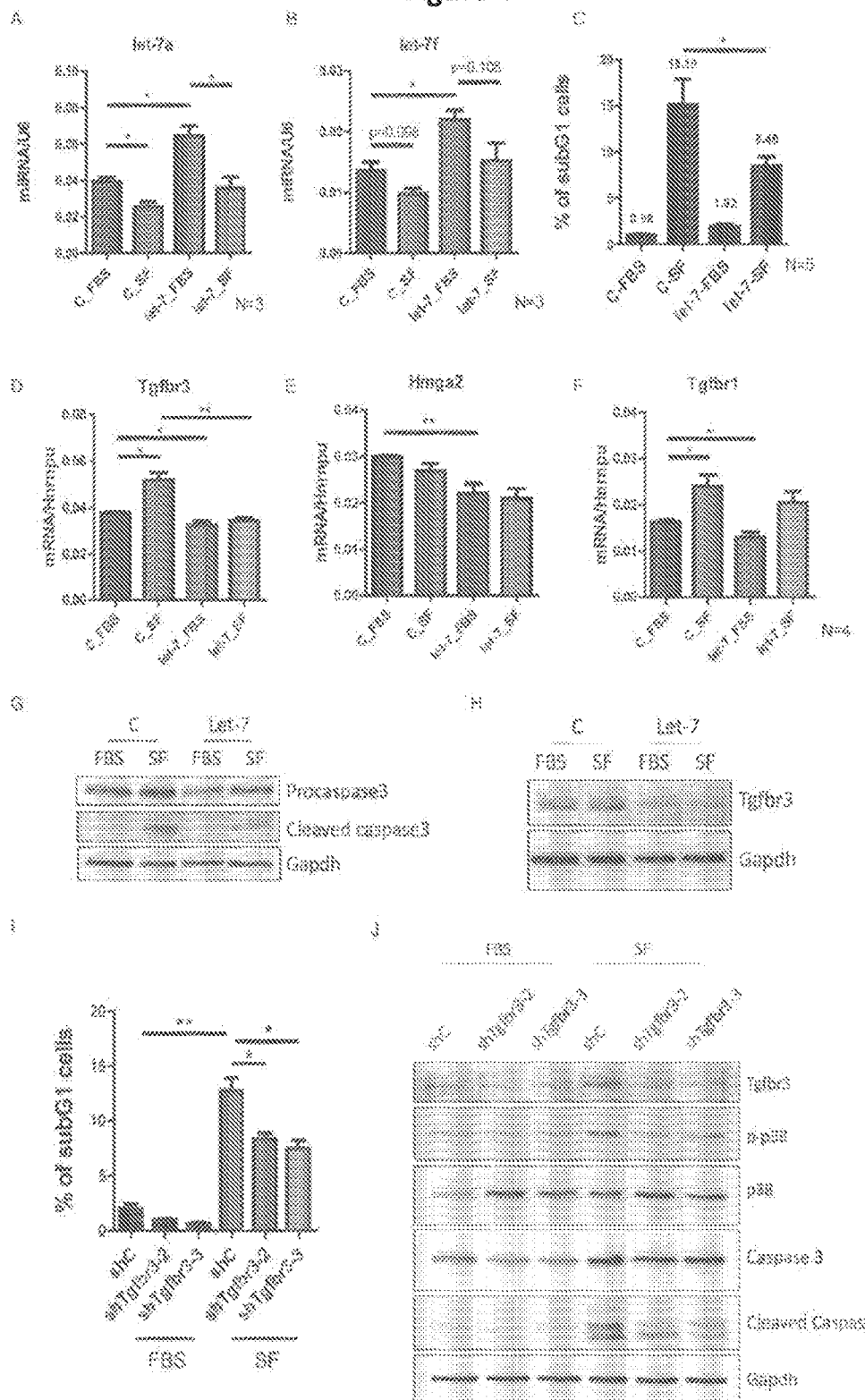
FIG. 4 shows let-7 overexpression and Tgfbr3 inhibition rescued serum depletion induced cell apoptosis. Panels A-B: Twenty-four-hour serum depletion downregulated let-7 expression and lentiviral mediated let-7 overexpression showed significant increase of let-7. Bars and error bars indicate mean and SEM from three independent experiments. Panel C: Serum depletion for 24 hours induced cell apoptosis by increase of subG1 population and let-7 overexpression rescued the effect. Bars and error bars indicate mean and SEM from five independent experiments. Panels D-F: Tgfbr3, Hmga2 and Tgfbr1 expression level under serum depletion and let-7 overexpression. Tgfbr3, Hmga2 and Tgfbr1 were significantly repressed by let-7 expression. Tgfbr3 and Tgfbr1 were induced by serum depletion. The induction of Tgfbr3 was repressed by let-7 overexpression under serum depletion. Bars and error bars indicate mean and SEM from four independent experiments. Panel G: Let-7 expression rescued serum free induced Caspase 3 activation. Panel H: Let-7 expression repressed Tgfbr3 induction by serum depletion. Panel I: Flow cytometry showed decreased subG1 population in shRNA mediated Tgfbr3 knockdown cells. Bars and error bars indicate mean and SEM from three independent experiments. Panel J: Western blot showed Tgfbr3 knockdown decreased activation of p38 MAPK and cleaved Caspases 3 under serum depletion stress.

(iv) Let-7 Overexpression and Inhibition of TGFBR3 Rescue Serum Free Induced Cell Apoptosis To investigate whether let-7 functions in cardiac protection under stress, let-7 overexpressing H9C2 cell line was generated by lentiviral infection and antibiotic selection. let-7 overexpressing H9C2 cell line significantly expressed both let-7a and let-7f (FIG. 4 Panels A and B). Serum depletion for 24 hours reduced let-7a expression in vitro (FIG. 4 Panel A), which might be due to the expression of Lin28 (FIG. 3 Panel G), and induced cell apoptosis (FIG. 4 Panels C and G). Overexpression of let-7 rescued serum depletion induced apoptosis in terms of subG1 population and expression of cleaved Caspase 3 (FIG. 4 Panels C and G). TGFBR3 was induced by serum depletion stress and be repressed by let-7 expression in terms of RNA and protein expression (FIG. 4 Panels D, H and J). Although let-7 overexpression significantly repressed Hmga2 and Tgfbr1 mRNA expression, the repression was not significant under serum depletion stress (FIG. 4 Panels E and F).

It was examined whether TGFBR3 is responsible for serum depletion induced cell apoptosis. Two shRNA mediated TGFBR3 knockdown cell lines were generated. The knockdown efficiency was confirmed under serum depletion (FIG. 4 Panel J). Both shRNA mediated TGFBR3 knockdown cell lines significantly rescued 24 hour-serum free induced cell apoptosis (FIG. 4 Panel I). Activated p38 MAPK and cleaved Caspase 3 were also reduced in these two TGFBR3 knockdown cell lines under serum depletion stress (FIG. 4 Panel J). These in vitro experiments indicate that let-7 plays a role in cardiac protection through inhibition of TGFBR3-p38 MAPK signaling pathway.

(v) Circulating Let-7 and TGFBR3 Response to Ischemic Cardiac Injury

Figure 5:
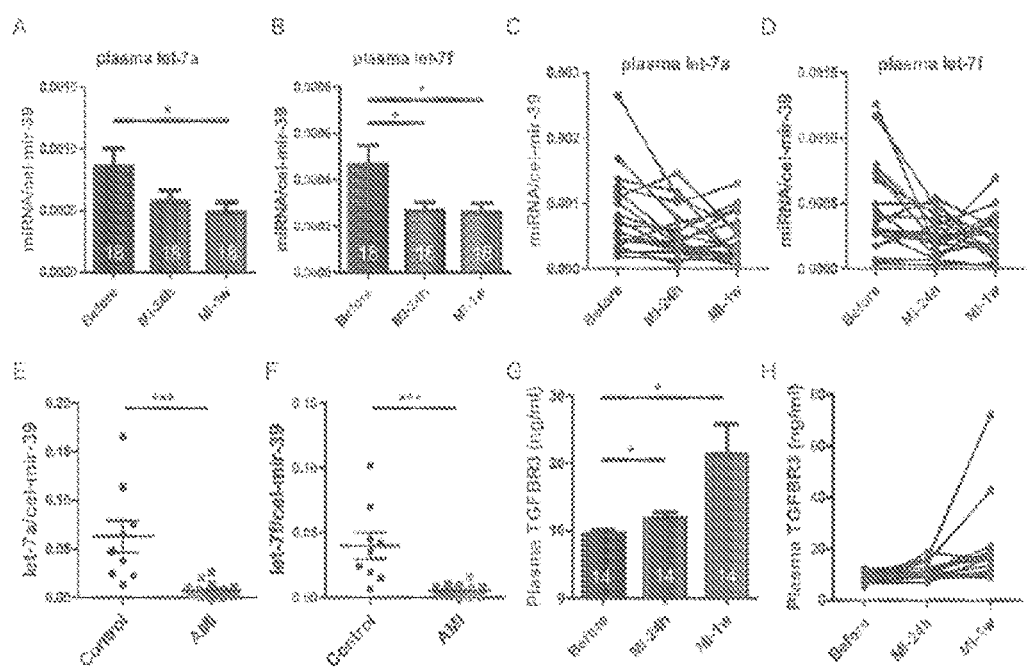
FIG. 5 shows circulating let-7 and TGFBR3 response to myocardial infarction. Panels A-D: Pig plasma let-7a and let-7f were significantly downregulated one week after LAD ligation. Plasma samples were collected before, 24 hours and one week post MI. Cel-mir-39 RNA was used as a spike-in control. Panels E-F: Human plasma let-7a and let-7f were significantly downregulated in acute myocardial infarction patients (n=25) comparing to healthy subjects (n=9). Panels G-H: Pig plasma TGFBR3 expression level measured by ELISA was significantly upregulated 24 hours and one week post MI.

Circulating miRNAs are important indicators for several diseases because of their stability and accessibility (Cortez et al., *Nat Rev Clin Oncol* 8, 467-477 (2011)). Therefore, it was evaluated whether plasma let-7 responds to ischemic injury. Pig plasma samples were collected before, 24-hour and one-week post LAD surgery. Plasma microRNA was extracted from these samples and both let-7a and let-7f were measured. Interestingly, both let-7a and let-7f were significantly downregulated one week after MI (FIG. 5 Panels A and B). Downregulation was also shown in individual pigs (FIG. 5 Panels C and D).

To further confirm these findings in clinical applications, plasma from acute MI patients was analyzed. In patients, plasma let-7a and let-7f expression were remarkably low comparing to control (FIG. 5 Panels E and F). These results indicate that the expression of circulating let-7a and let-7f may respond to tissue injury after myocardial infarction.

TGFBR3 is a membrane protein, but also can be cleaved and released into the extracellular matrix (Bilandzic et al., *Mol Cell Endocrinol* 339, 180-189 (2011)). It is possible that upregulation of TGFBR3 in tissues may lead to increase the concentration of TGFBR3 in the plasma. The concentration of pig plasma TGFBR3 was thus analyzed. The basal level of TGFBR3 was around 10 ng/ml in pig plasma (FIG. 5 Panels G and H). Twenty-four-hours and one-week post MI, the level of plasma TGFBR3 was significantly upregulated (FIG. 5 Panel G). For each individual pig, increased plasma TGFBR3 was also observed (FIG. 5 Panel H). These data suggest the differential expression of microRNAs, let-7a and let-7f, and their target gene, TGFBR3, are able to be detected in the plasma. They may be serve as therapeutic targets or biomarkers for further investigation.

Using large animal model and next generation sequencing technique, this study demonstrated that let-7a and let-7f were ischemic cardiac injury effectors. The downregulation of these microRNAs lead to de-repression of TGFBR3 expression. In cardiomyocytes, TGFBR3 mediates p38 MAPK activation and cell apoptosis. Both expression of let-7 and inhibition of TGFBR3 rescued stress induced cell apoptosis. Surprisingly, the downregulation of let-7 and the upregulation of TGFBR3 could be detected in the plasma after MI, indicating that such microRNAs can serve as reliable biomarkers for early stage MI detection.

The results from this study indicate that microRNA let-7/TGFBR3 axis mediates ischemic induced cell apoptosis through p38 MAPK activation. Plasma microRNA let-7a and let-7f, as well as plasma TGFBR3 are responsive to heart injury. Thus, these microRNAs and their target genes such as TGFBR3 are not only expected to be potential therapeutic targets, but also expected to be potential biomarkers for diagnosis.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for treating a cardiac injury, comprising administering to a subject in need thereof an effective amount of an enhancer of let-7a and/or let-7f or a transformation growth factor beta receptor III (TGFBR3) inhibitor to reduce the biological activity of TGFBR3, wherein the TGFBR3 inhibitor is an interfering RNA (RNAi) or an Anti-RIII-1 antibody that comprises the same heavy chain complementary determining regions (CDRs) as those in SEQ ID NO: 95 and the same light chain CDRs as those in SEQ ID NO: 96.

2. The method of claim 1, wherein the TGFBR3 inhibitor is an antibody binding to TGFBR3.

3. The method of claim 1, wherein the antibody comprises a heavy chain variable region having the amino acid sequence of SEQ ID NO: 95 and a light chain variable region having the amino acid sequence of SEQ ID NO:96.

4. The method of claim 2, wherein the antibody is a full-length antibody or an antigen-binding fragment thereof.

5. The method of claim 2, wherein the antibody is a human antibody, a humanized antibody, a chimeric antibody, or a single-chain antibody.

6. The method of claim 1, wherein the let-7 enhancer is a let-7 nucleic acid.

7. The method of claim 6, wherein the let-7 nucleic acid comprises the nucleotide sequence of SEQ ID NO: 94.

8. The method of claim 1, wherein the subject is a human patient having or suspected of having the cardiac injury.

9. The method of claim 1, wherein the subject is a human patient having or suspected of having myocardial infarction.

10. The method of claim 1, wherein the subject has an elevated level of TGFBR3, a reduced level of let-7, or both as compared to a subject not suffering from the cardiac injury.

11. The method of claim 1, wherein the let-7 enhancer or the TGFBR3 inhibitor is delivered by a systemic route or by a local route.

12. The method of claim 11, wherein the local route is intramyocardial injection or intracoronary injection.

13. The method of claim 8 further comprising:
(i) providing a biological sample suspected of containing TGFBR3 from the subject,
(ii) contacting the biological sample with an antibody that binds a cleaved form of TGFBR3, which comprises the amino acid sequence of SEQ ID NO:3
(iii) measuring the level of the cleaved form of TGFBR3 in the biological sample; and
(iv) determining the presence or absence of TGFBR3 in the biological sample.

14. The method of claim 13, wherein the antibody specifically binds glycosylated SEQ ID NO: 3.

15. The method of claim 14, wherein the antibody binds an N-terminal epitope of SEQ ID NO: 3, wherein the epitope is glycosylated.

16. The method of claim 13, wherein the biological sample is obtained from a human subject suspected of having a cardiac injury.

17. The method of claim 13, wherein the biological sample is a serum sample or a plasma sample.

18. The method of claim 13, wherein the method further comprises measuring the level of let-7 in the biological sample.

19. The method of claim 1, wherein the biological activity of TGFBR3 is reduced by 20-500%.

20. The method of claim 13, wherein in (iii), the level of the cleaved form of TGFBR3 is 1%-500% more as compared to a subject not suffering from cardiac injury.

21. The method of claim 1, wherein the cardiac injury involves myocardial infarction, an acute coronary syndrome, myocarditis, cardiomyopathy, or a post-operation injury.

* * * * *

UNITED STATES PATENT AND TRADEMARK OFFICE
CERTIFICATE OF CORRECTION

PATENT NO. : 11,246,883 B2
APPLICATION NO. : 16/337583
DATED : February 15, 2022
INVENTOR(S) : Patrick C. H. Hsieh et al.

It is certified that error appears in the above-identified patent and that said Letters Patent is hereby corrected as shown below:

In the Claims

In Claim 13, Column 80, Lines 34-43:
"13. The method of claim 8 further comprising:
    (i) providing a biological sample suspected of containing TGFBR3 from the subject,
    (ii) contacting the biological sample with an antibody that binds a cleaved form of TGFBR3, which comprises the amino acid sequence of SEQ ID NO:3
    (iii) measuring the level of the cleaved form of TGFBR3 in the biological sample; and
    (iv) determining the presence or absence of TGFBR3 in the biological sample."

Should read:
--13. The method of claim 8 further comprising:
    (i) providing a biological sample suspected of containing TGFBR3 from the subject;
    (ii) contacting the biological sample with an antibody that binds a cleaved form of TGFBR3, which comprises the amino acid sequence of SEQ ID NO:3;
    (iii) measuring the level of the cleaved form of TGFBR3 in the biological sample; and
    (iv) determining the presence or absence of TGFBR3 in the biological sample.--

Signed and Sealed this
Tenth Day of May, 2022

Katherine Kelly Vidal
*Director of the United States Patent and Trademark Office*

SEQUENCE LISTING

```
<160> NUMBER OF SEQ ID NOS: 96

<210> SEQ ID NO 1
<211> LENGTH: 831
<212> TYPE: PRT
<213> ORGANISM: Homo sapiens

<400> SEQUENCE: 1

Gly Pro Glu Pro Gly Ala Leu Cys Glu Leu Ser Pro Val Ser Ala Ser
1               5                   10                  15

His Pro Val Gln Ala Leu Met Glu Ser Phe Thr Val Leu Ser Gly Cys
            20                  25                  30

Ala Ser Arg Gly Thr Thr Gly Leu Pro Gln Glu Val His Val Leu Asn
        35                  40                  45

Leu Arg Thr Ala Gly Gln Gly Pro Gly Gln Leu Gln Arg Glu Val Thr
    50                  55                  60

Leu His Leu Asn Pro Ile Ser Ser Val His Ile His His Lys Ser Val
65                  70                  75                  80

Val Phe Leu Leu Asn Ser Pro His Pro Leu Val Trp His Leu Lys Thr
                85                  90                  95

Glu Arg Leu Ala Thr Gly Val Ser Arg Leu Phe Leu Val Ser Glu Gly
            100                 105                 110

Ser Val Val Gln Phe Ser Ser Ala Asn Phe Ser Leu Thr Ala Glu Thr
        115                 120                 125
```

```
Glu Glu Arg Asn Phe Pro His Gly Asn Glu His Leu Leu Asn Trp Ala
    130                 135                 140
Arg Lys Glu Tyr Gly Ala Val Thr Ser Phe Thr Glu Leu Lys Ile Ala
145                 150                 155                 160
Arg Asn Ile Tyr Ile Lys Val Gly Glu Asp Gln Val Phe Pro Pro Lys
                165                 170                 175
Cys Asn Ile Gly Lys Asn Phe Leu Ser Leu Asn Tyr Leu Ala Glu Tyr
                180                 185                 190
Leu Gln Pro Lys Ala Ala Glu Gly Cys Val Met Ser Ser Gln Pro Gln
            195                 200                 205
Asn Glu Glu Val His Ile Ile Glu Leu Ile Thr Pro Asn Ser Asn Pro
    210                 215                 220
Tyr Ser Ala Phe Gln Val Asp Ile Thr Ile Asp Ile Arg Pro Ser Gln
225                 230                 235                 240
Glu Asp Leu Glu Val Val Lys Asn Leu Ile Leu Ile Leu Lys Cys Lys
                245                 250                 255
Lys Ser Val Asn Trp Val Ile Lys Ser Phe Asp Val Lys Gly Ser Leu
                260                 265                 270
Lys Ile Ile Ala Pro Asn Ser Ile Gly Phe Gly Lys Glu Ser Glu Arg
            275                 280                 285
Ser Met Thr Met Thr Lys Ser Ile Arg Asp Asp Ile Pro Ser Thr Gln
    290                 295                 300
Gly Asn Leu Val Lys Trp Ala Leu Asp Asn Gly Tyr Ser Pro Ile Thr
305                 310                 315                 320
Ser Tyr Thr Met Ala Pro Val Ala Asn Arg Phe His Leu Arg Leu Glu
                325                 330                 335
Asn Asn Ala Glu Glu Met Gly Asp Glu Val His Thr Ile Pro Pro
            340                 345                 350
Glu Leu Arg Ile Leu Leu Asp Pro Gly Ala Leu Pro Ala Leu Gln Asn
    355                 360                 365
Pro Pro Ile Arg Gly Gly Glu Gly Gln Asn Gly Gly Leu Pro Phe Pro
370                 375                 380
Phe Pro Asp Ile Ser Arg Arg Val Trp Asn Glu Glu Gly Glu Asp Gly
385                 390                 395                 400
Leu Pro Arg Pro Lys Asp Pro Val Ile Pro Ser Ile Gln Leu Phe Pro
                405                 410                 415
Gly Leu Arg Glu Pro Glu Glu Val Gln Gly Ser Val Asp Ile Ala Leu
            420                 425                 430
Ser Val Lys Cys Asp Asn Glu Lys Met Ile Val Ala Val Glu Lys Asp
    435                 440                 445
Ser Phe Gln Ala Ser Gly Tyr Ser Gly Met Asp Val Thr Leu Leu Asp
    450                 455                 460
Pro Thr Cys Lys Ala Lys Met Asn Gly Thr His Phe Val Leu Glu Ser
465                 470                 475                 480
Pro Leu Asn Gly Cys Gly Thr Arg Pro Arg Trp Ser Ala Leu Asp Gly
                485                 490                 495
Val Val Tyr Tyr Asn Ser Ile Val Ile Gln Val Pro Ala Leu Gly Asp
                500                 505                 510
Ser Ser Gly Trp Pro Asp Gly Tyr Glu Asp Leu Glu Ser Gly Asp Asn
            515                 520                 525
Gly Phe Pro Gly Asp Met Asp Glu Gly Asp Ala Ser Leu Phe Thr Arg
530                 535                 540
```

```
Pro Glu Ile Val Val Phe Asn Cys Ser Leu Gln Gln Val Arg Asn Pro
545                 550                 555                 560

Ser Ser Phe Gln Glu Gln Pro His Gly Asn Ile Thr Phe Asn Met Glu
            565                 570                 575

Leu Tyr Asn Thr Asp Leu Phe Leu Val Pro Ser Gln Gly Val Phe Ser
            580                 585                 590

Val Pro Glu Asn Gly His Val Tyr Val Glu Val Ser Val Thr Lys Ala
            595                 600                 605

Glu Gln Glu Leu Gly Phe Ala Ile Gln Thr Cys Phe Ile Ser Pro Tyr
            610                 615                 620

Ser Asn Pro Asp Arg Met Ser His Tyr Thr Ile Ile Glu Asn Ile Cys
625                 630                 635                 640

Pro Lys Asp Glu Ser Val Lys Phe Tyr Ser Pro Lys Arg Val His Phe
            645                 650                 655

Pro Ile Pro Gln Ala Asp Met Asp Lys Lys Arg Phe Ser Phe Val Phe
            660                 665                 670

Lys Pro Val Phe Asn Thr Ser Leu Leu Phe Leu Gln Cys Glu Leu Thr
            675                 680                 685

Leu Cys Thr Lys Met Glu Lys His Pro Gln Lys Leu Pro Lys Cys Val
690                 695                 700

Pro Pro Asp Glu Ala Cys Thr Ser Leu Asp Ala Ser Ile Ile Trp Ala
705                 710                 715                 720

Met Met Gln Asn Lys Lys Thr Phe Thr Lys Pro Leu Ala Val Ile His
            725                 730                 735

His Glu Ala Glu Ser Lys Glu Lys Gly Pro Ser Met Lys Glu Pro Asn
            740                 745                 750

Pro Ile Ser Pro Pro Ile Phe His Gly Leu Asp Thr Leu Thr Val Met
            755                 760                 765

Gly Ile Ala Phe Ala Ala Phe Val Ile Gly Ala Leu Leu Thr Gly Ala
            770                 775                 780

Leu Trp Tyr Ile Tyr Ser His Thr Gly Glu Thr Ala Gly Arg Gln Gln
785                 790                 795                 800

Val Pro Thr Ser Pro Pro Ala Ser Glu Asn Ser Ser Ala Ala His Ser
            805                 810                 815

Ile Gly Ser Thr Gln Ser Thr Pro Cys Ser Ser Ser Thr Ala
            820                 825                 830

<210> SEQ ID NO 2
<211> LENGTH: 64
<212> TYPE: PRT
<213> ORGANISM: Homo sapiens

<400> SEQUENCE: 2

Met Gly Ile Ala Phe Ala Ala Phe Val Ile Gly Ala Leu Leu Thr Gly
1               5                   10                  15

Ala Leu Trp Tyr Ile Tyr Ser His Thr Gly Glu Thr Ala Gly Arg Gln
            20                  25                  30

Gln Val Pro Thr Ser Pro Pro Ala Ser Glu Asn Ser Ser Ala Ala His
        35                  40                  45

Ser Ile Gly Ser Thr Gln Ser Thr Pro Cys Ser Ser Ser Thr Ala
    50                  55                  60

<210> SEQ ID NO 3
<211> LENGTH: 767
<212> TYPE: PRT
<213> ORGANISM: Homo sapiens
```

<400> SEQUENCE: 3

```
Gly Pro Glu Pro Gly Ala Leu Cys Glu Leu Ser Pro Val Ser Ala Ser
1               5                   10                  15

His Pro Val Gln Ala Leu Met Glu Ser Phe Thr Val Leu Ser Gly Cys
            20                  25                  30

Ala Ser Arg Gly Thr Thr Gly Leu Pro Gln Glu Val His Val Leu Asn
        35                  40                  45

Leu Arg Thr Ala Gly Gln Gly Pro Gly Gln Leu Gln Arg Glu Val Thr
    50                  55                  60

Leu His Leu Asn Pro Ile Ser Ser Val His Ile His His Lys Ser Val
65                  70                  75                  80

Val Phe Leu Leu Asn Ser Pro His Pro Leu Val Trp His Leu Lys Thr
                85                  90                  95

Glu Arg Leu Ala Thr Gly Val Ser Arg Leu Phe Leu Val Ser Glu Gly
            100                 105                 110

Ser Val Val Gln Phe Ser Ser Ala Asn Phe Ser Leu Thr Ala Glu Thr
        115                 120                 125

Glu Glu Arg Asn Phe Pro His Gly Asn Glu His Leu Leu Asn Trp Ala
    130                 135                 140

Arg Lys Glu Tyr Gly Ala Val Thr Ser Phe Thr Glu Leu Lys Ile Ala
145                 150                 155                 160

Arg Asn Ile Tyr Ile Lys Val Gly Glu Asp Gln Val Phe Pro Pro Lys
                165                 170                 175

Cys Asn Ile Gly Lys Asn Phe Leu Ser Leu Asn Tyr Leu Ala Glu Tyr
            180                 185                 190

Leu Gln Pro Lys Ala Ala Glu Gly Cys Val Met Ser Ser Gln Pro Gln
        195                 200                 205

Asn Glu Glu Val His Ile Ile Glu Leu Ile Thr Pro Asn Ser Asn Pro
    210                 215                 220

Tyr Ser Ala Phe Gln Val Asp Ile Thr Ile Asp Ile Arg Pro Ser Gln
225                 230                 235                 240

Glu Asp Leu Glu Val Val Lys Asn Leu Ile Leu Ile Leu Lys Cys Lys
                245                 250                 255

Lys Ser Val Asn Trp Val Ile Lys Ser Phe Asp Val Lys Gly Ser Leu
            260                 265                 270

Lys Ile Ile Ala Pro Asn Ser Ile Gly Phe Gly Lys Glu Ser Glu Arg
        275                 280                 285

Ser Met Thr Met Thr Lys Ser Ile Arg Asp Asp Ile Pro Ser Thr Gln
    290                 295                 300

Gly Asn Leu Val Lys Trp Ala Leu Asp Asn Gly Tyr Ser Pro Ile Thr
305                 310                 315                 320

Ser Tyr Thr Met Ala Pro Val Ala Asn Arg Phe His Leu Arg Leu Glu
                325                 330                 335

Asn Asn Ala Glu Glu Met Gly Asp Glu Glu Val His Thr Ile Pro Pro
            340                 345                 350

Glu Leu Arg Ile Leu Leu Asp Pro Gly Ala Leu Pro Ala Leu Gln Asn
        355                 360                 365

Pro Pro Ile Arg Gly Gly Glu Gly Gln Asn Gly Leu Pro Phe Pro
    370                 375                 380

Phe Pro Asp Ile Ser Arg Arg Val Trp Asn Glu Glu Gly Glu Asp Gly
385                 390                 395                 400

Leu Pro Arg Pro Lys Asp Pro Val Ile Pro Ser Ile Gln Leu Phe Pro
```

```
                    405                 410                 415
Gly Leu Arg Glu Pro Glu Val Gln Gly Ser Val Asp Ile Ala Leu
                420                 425                 430

Ser Val Lys Cys Asp Asn Glu Lys Met Ile Val Ala Val Glu Lys Asp
            435                 440                 445

Ser Phe Gln Ala Ser Gly Tyr Ser Gly Met Asp Val Thr Leu Leu Asp
        450                 455                 460

Pro Thr Cys Lys Ala Lys Met Asn Gly Thr His Phe Val Leu Glu Ser
465                 470                 475                 480

Pro Leu Asn Gly Cys Gly Thr Arg Pro Arg Trp Ser Ala Leu Asp Gly
                485                 490                 495

Val Val Tyr Tyr Asn Ser Ile Val Ile Gln Val Pro Ala Leu Gly Asp
            500                 505                 510

Ser Ser Gly Trp Pro Asp Gly Tyr Glu Asp Leu Glu Ser Gly Asp Asn
        515                 520                 525

Gly Phe Pro Gly Asp Met Asp Glu Gly Asp Ala Ser Leu Phe Thr Arg
    530                 535                 540

Pro Glu Ile Val Val Phe Asn Cys Ser Leu Gln Gln Val Arg Asn Pro
545                 550                 555                 560

Ser Ser Phe Gln Glu Gln Pro His Gly Asn Ile Thr Phe Asn Met Glu
                565                 570                 575

Leu Tyr Asn Thr Asp Leu Phe Leu Val Pro Ser Gln Gly Val Phe Ser
            580                 585                 590

Val Pro Glu Asn Gly His Val Tyr Val Glu Val Ser Val Thr Lys Ala
        595                 600                 605

Glu Gln Glu Leu Gly Phe Ala Ile Gln Thr Cys Phe Ile Ser Pro Tyr
    610                 615                 620

Ser Asn Pro Asp Arg Met Ser His Tyr Thr Ile Ile Glu Asn Ile Cys
625                 630                 635                 640

Pro Lys Asp Glu Ser Val Lys Phe Tyr Ser Pro Lys Arg Val His Phe
                645                 650                 655

Pro Ile Pro Gln Ala Asp Met Asp Lys Lys Arg Phe Ser Phe Val Phe
            660                 665                 670

Lys Pro Val Phe Asn Thr Ser Leu Leu Phe Leu Gln Cys Glu Leu Thr
        675                 680                 685

Leu Cys Thr Lys Met Glu Lys His Pro Gln Lys Leu Pro Lys Cys Val
    690                 695                 700

Pro Pro Asp Glu Ala Cys Thr Ser Leu Asp Ala Ser Ile Ile Trp Ala
705                 710                 715                 720

Met Met Gln Asn Lys Lys Thr Phe Thr Lys Pro Leu Ala Val Ile His
                725                 730                 735

His Glu Ala Glu Ser Lys Glu Lys Gly Pro Ser Met Lys Glu Pro Asn
            740                 745                 750

Pro Ile Ser Pro Pro Ile Phe His Gly Leu Asp Thr Leu Thr Val
        755                 760                 765

<210> SEQ ID NO 4
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 4
ctcaactggt gtcgtggagt cggcaattca gttgagaact atac                              44
```

<210> SEQ ID NO 5
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 5
ctcaactggt gtcgtggagt cggcaattca gttgagacag ttct    44

<210> SEQ ID NO 6
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 6
ctcaactggt gtcgtggagt cggcaattca gttgagttca gtta    44

<210> SEQ ID NO 7
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 7
ctcaactggt gtcgtggagt cggcaattca gttgagtcat agcc    44

<210> SEQ ID NO 8
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 8
ctcaactggt gtcgtggagt cggcaattca gttgagtaac caat    44

<210> SEQ ID NO 9
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 9
acactccagc tgggtgaggt agtagrttgt    30

<210> SEQ ID NO 10
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 10
acactccagc tgggaagctg cca    23

<210> SEQ ID NO 11
<211> LENGTH: 29
<212> TYPE: DNA
<213> ORGANISM: Artificial Sequence
<220> FEATURE:

<223> OTHER INFORMATION: Synthetic Polynucleotide

<400> SEQUENCE: 11
acactccagc tgggtacagt actgtgata                                    29

<210> SEQ ID NO 12
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 12
acactccagc tgggagcagc attgtacagg g                                 31

<210> SEQ ID NO 13
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 13
acactccagc tgggacagta gtctgcacat                                   30

<210> SEQ ID NO 14
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 14
gtttgccccc atagcactct                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 15
tggactcctc ctaaagccga                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 16
ggtatgagcc acgggaagag                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 17
caagctcgcc atgttgactg                                              20

```
<210> SEQ ID NO 18
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 18
gggggagatg tgcagaaaca                                                   20

<210> SEQ ID NO 19
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 19
atggctctca gcctttggac                                                   20

<210> SEQ ID NO 20
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 20
ggggagttac cagagtgtgc                                                   20

<210> SEQ ID NO 21
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 21
cctccaagga ggatatgaag cg                                                22

<210> SEQ ID NO 22
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 22
tcctcaacaa ggagctgatg c                                                 21

<210> SEQ ID NO 23
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 23
actgtgggca aaccgatcaa                                                   20

<210> SEQ ID NO 24
<211> LENGTH: 20
<212> TYPE: DNA
<213> ORGANISM: Artificial Sequence
<220> FEATURE:
<223> OTHER INFORMATION: Synthetic Polynucleotide
```

<400> SEQUENCE: 24
agagacccag aggaagaccc          20

<210> SEQ ID NO 25
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 25
tttcgaggat gtgtcccagc          20

<210> SEQ ID NO 26
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 26
tggcgcctga ggtactaaga          20

<210> SEQ ID NO 27
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 27
ggtctgtgtt ggcgtcagta          20

<210> SEQ ID NO 28
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 28
aaagcgagag cctcggaaac          20

<210> SEQ ID NO 29
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 29
agggaatgga tacggcaacc          20

<210> SEQ ID NO 30
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 30
aggcagtctg tacgggtttg          20

<210> SEQ ID NO 31
<211> LENGTH: 20

```
<210> SEQ ID NO 31
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 31
tggcactcaa ggctgtatgg                                               20

<210> SEQ ID NO 32
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 32
tcttcgtcca cacgcctaac                                               20

<210> SEQ ID NO 33
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 33
cggcgttgaa aacaaggagg                                               20

<210> SEQ ID NO 34
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 34
gggacgaata ccgcagagag                                               20

<210> SEQ ID NO 35
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 35
gactggatga aggcgacaca                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 36
gtggtgaccc tcaagaccag                                               20

<210> SEQ ID NO 37
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 37
```
gagagccaag cacctccg                                          18

<210> SEQ ID NO 38
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 38
gcgtttggat gaagcacagg                                        20

<210> SEQ ID NO 39
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 39
tccaaaccac agagtaggca c                                      21

<210> SEQ ID NO 40
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 40
agacattcac caagcccctg                                        20

<210> SEQ ID NO 41
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 41
ggacttggcc ttgcaggtta                                        20

<210> SEQ ID NO 42
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 42
ggcaattccg atgactgtcc                                        20

<210> SEQ ID NO 43
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 43
cttcgagcgg agctatggag                                        20

<210> SEQ ID NO 44
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 44
cctacctccc aatctcccga                                               20

<210> SEQ ID NO 45
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 45
tgacctaatt ccgcgagaca                                               20

<210> SEQ ID NO 46
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 46
gagtacctcc agcccaaacc                                               20

<210> SEQ ID NO 47
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 47
cagacagcat catccaagca tc                                            22

<210> SEQ ID NO 48
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 48
ttctgcattg ggagcgagag                                               20

<210> SEQ ID NO 49
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 49
cctagagtgc ccaccttgtg                                               20

<210> SEQ ID NO 50
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 50
cgtgtccttc agtcctgctt                                               20

<210> SEQ ID NO 51
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 51
taatgatcgg tcagtgcgtc c                                              21

<210> SEQ ID NO 52
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 52
agctgctgaa acccttctt t                                               21

<210> SEQ ID NO 53
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 53
gtttattacc ggctggctgc                                                20

<210> SEQ ID NO 54
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 54
agttcaacag ctcgaagggg                                                20

<210> SEQ ID NO 55
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 55
cttctgacgc tctgcatcct                                                20

<210> SEQ ID NO 56
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 56
agagaggggt gctacaggag                                                20

<210> SEQ ID NO 57
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 57
gcactcgcag gaagtgagat                                              20

<210> SEQ ID NO 58
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 58
ccacctcccg gttgactct                                               19

<210> SEQ ID NO 59
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 59
ttgttgtggc catttcctgg                                              20

<210> SEQ ID NO 60
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 60
gcgcatgact gcctcaaaaa                                              20

<210> SEQ ID NO 61
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 61
cgggatggat ggtgcagtag                                              20

<210> SEQ ID NO 62
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 62
gcggggtatc tgactctgtg                                              20

<210> SEQ ID NO 63
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 63
atacaacggg acttctccga c                                            21

<210> SEQ ID NO 64

```
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 64
acatcctcag acactgatgg c                                              21

<210> SEQ ID NO 65
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 65
ggcttgtcct tgcctaaggt                                                20

<210> SEQ ID NO 66
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 66
gggcatcagt gaggcttgaa                                                20

<210> SEQ ID NO 67
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 67
actgctctgg tactgttgcc                                                20

<210> SEQ ID NO 68
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 68
ccttggcaaa ttccgtgagc                                                20

<210> SEQ ID NO 69
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 69
cggcgctctt caattgcttt                                                20

<210> SEQ ID NO 70
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 70
```
tctgcagcag tgaaagctca                                              20

<210> SEQ ID NO 71
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 71
ccatgaagga acccgttgga                                              20

<210> SEQ ID NO 72
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 72
atatccacca ccgaggggaa                                              20

<210> SEQ ID NO 73
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 73
acccttTgtt ccagctctcg                                              20

<210> SEQ ID NO 74
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 74
tggattccgc caatggaaca                                              20

<210> SEQ ID NO 75
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 75
cgctccgatc acaaatgctg                                              20

<210> SEQ ID NO 76
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 76
ccaacagcct tgcccaaatg                                              20

<210> SEQ ID NO 77
<211> LENGTH: 20
<212> TYPE: DNA

<213> ORGANISM: Artificial Sequence
<220> FEATURE:
<223> OTHER INFORMATION: Synthetic Polynucleotide

<400> SEQUENCE: 77
gggatccctg cttgcttctt                                          20

<210> SEQ ID NO 78
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 78
gcttgacacg agtcctctct                                          20

<210> SEQ ID NO 79
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 79
gtcctctctt ctgaggcacc                                          20

<210> SEQ ID NO 80
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 80
gccagatggt ggctttcctg                                          20

<210> SEQ ID NO 81
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 81
cctggaaagc actgtagggg                                          20

<210> SEQ ID NO 82
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 82
taaaagtatc cccacccaac ctg                                      23

<210> SEQ ID NO 83
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 83
gcagtttgca ttccttggca                                          20

<210> SEQ ID NO 84
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 84
ccaaaaggcc tggtcctaga                                               20

<210> SEQ ID NO 85
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 85
aaaggcctgg tcctaga                                                  17

<210> SEQ ID NO 86
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 86
ctgtagacaa agactctttc                                               20

<210> SEQ ID NO 87
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 87
cattgcattt gcagcatttg                                               20

<210> SEQ ID NO 88
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 88
ctggtgtcgt ggagtcggca attc                                          24

<210> SEQ ID NO 89
<211> LENGTH: 80
<212> TYPE: RNA
<213> ORGANISM: Homo sapiens

<400> SEQUENCE: 89
ugggaugagg uaguagguug uauaguuuua gggucacacc caccacuggg agauaacuau   60
acaaucuacu gucuuuccua                                               80

<210> SEQ ID NO 90
<211> LENGTH: 72
<212> TYPE: RNA
<213> ORGANISM: Homo sapiens

```
<400> SEQUENCE: 90
agguugaggu aguagguugu auaguuuaga auuacaucaa gggagauaac uguacagccu    60
ccuagcuuuc cu                                                        72

<210> SEQ ID NO 91
<211> LENGTH: 74
<212> TYPE: RNA
<213> ORGANISM: Homo sapiens

<400> SEQUENCE: 91
gggugaggua guagguugua uaguuugggg cucugcccug cuaugggaua acuauacaau    60
cuacugucuu uccu                                                      74

<210> SEQ ID NO 92
<211> LENGTH: 87
<212> TYPE: RNA
<213> ORGANISM: Homo sapiens

<400> SEQUENCE: 92
ucagagugag guaguagauu guauaguugu ggggaguaguga uuuuacccug uucaggagau   60
aacuauacaa ucuauugccu ucccuga                                        87

<210> SEQ ID NO 93
<211> LENGTH: 83
<212> TYPE: RNA
<213> ORGANISM: Homo sapiens

<400> SEQUENCE: 93
ugugggauga gguaguagau uguauaguuu uagggucaua ccccaucuug gagauaacua    60 uacagcuac ugucuuuccc acg                                             83

<210> SEQ ID NO 94
<211> LENGTH: 22
<212> TYPE: RNA
<213> ORGANISM: Homo sapiens

<400> SEQUENCE: 94
ugagguagua gguuguauag uu                                             22

<210> SEQ ID NO 95
<211> LENGTH: 115
<212> TYPE: PRT
<213> ORGANISM: Homo sapiens

<400> SEQUENCE: 95
```

Val Val Glu Ser Gly Gly Gly Leu Val Lys Pro Gly Gly Ser Leu Lys
1               5                   10                  15

Leu Ser Cys Ala Ala Ser Gly Phe Thr Phe Ser Asp Tyr Tyr Met Tyr
            20                  25                  30

Trp Val Arg Gln Thr Pro Glu Lys Arg Leu Glu Trp Val Ala Thr Ile
        35                  40                  45

Ser Asp Gly Gly Ser Tyr Thr Tyr Tyr Pro Asp Ser Val Lys Gly Arg
    50                  55                  60

Phe Thr Ile Ser Arg Asp Asn Ala Lys Asn Asn Leu Tyr Leu Gln Met
65                  70                  75                  80

Ser Ser Leu Lys Ser Glu Asp Thr Ala Met Tyr Tyr Cys Ala Arg Asp
                85                  90                  95

Gly Asn Tyr Trp Tyr Phe Asp Val Trp Gly Ala Gly Thr Thr Val Thr

```
                        100                 105                 110

Val Ser Ser
        115

<210> SEQ ID NO 96
<211> LENGTH: 104
<212> TYPE: PRT
<213> ORGANISM: Homo sapiens

<400> SEQUENCE: 96

Gln Ser Val Gln Ser Pro Ser Ser Leu Ser Ala Ser Leu Gly Gly Lys
1               5                   10                  15

Val Thr Ile Thr Cys Lys Ala Ser Gln Asp Ile Asn Lys Tyr Ile Ala
            20                  25                  30

Trp Tyr Gln His Lys Pro Gly Lys Gly Pro Arg Leu Leu Ile His Tyr
        35                  40                  45

Thr Ser Thr Leu Gln Pro Gly Ile Pro Ser Arg Phe Ser Gly Ser Gly
    50                  55                  60

Ser Gly Arg Asp Tyr Ser Phe Ser Ile Ser Asn Leu Glu Pro Glu Asp
65                  70                  75                  80

Ile Ala Thr Tyr Tyr Cys Leu Gln Tyr Asp Asn Leu Arg Thr Phe Gly
                85                  90                  95

Gly Gly Thr Lys Leu Glu Ile Lys
            100
```